(12) United States Patent
Verhoeyen

(10) Patent No.: US 6,204,366 B1
(45) Date of Patent: Mar. 20, 2001

(54) SPECIFIC BINDING AGENTS

(75) Inventor: Martine Elisa Verhoeyen, Rushden (GB)

(73) Assignee: Unilever Patent Holdings B.V., Rotterdam (NL)

( * ) Notice: Subject to any disclaimer, the term of this patent is extended or adjusted under 35 U.S.C. 154(b) by 0 days.

(21) Appl. No.: 07/987,264

(22) PCT Filed: Sep. 5, 1991

(86) PCT No.: PCT/GB91/01511

§ 371 Date: May 7, 1993

§ 102(e) Date: May 7, 1993

(87) PCT Pub. No.: WO92/04380

PCT Pub. Date: Mar. 19, 1992

(30) Foreign Application Priority Data

Sep. 7, 1990 (GB) .................................. 9019553

(51) Int. Cl.[7] .................................. A61K 39/395
(52) U.S. Cl. .................. 530/387.3; 530/387.5; 530/387.7; 424/133.1; 424/137.1; 424/138.1; 435/69.6; 435/69.7; 435/91.1; 435/328; 435/329; 435/330; 536/23.4; 536/23.53
(58) Field of Search ................ 536/23.53, 23.4; 530/387.1, 867, 866, 387.3, 387.5, 387.7; 435/69.1, 91.1, 320.1, 252.3, 253.33, 69.7, 328, 329, 330; 424/133.1, 133.7, 138.1

(56) References Cited

FOREIGN PATENT DOCUMENTS 0 239 400 * 9/1987 (EP) .............................. C12N/15/00
369816   5/1990 (EP) .

OTHER PUBLICATIONS

Queen et al. [PNAS 86:10029–10033 (1989)].*
Taylor–Papadimitriou et al. [Int. J. Cancer 28:23–29 (1981)].*
Arklie et al. [Int. J. Cancer 28:23–29 (1981)].*
Riechmann et al. [Nature 332:323–327 (1988)].*
WO,A,8907268, Aug. 1989, John Muir Cancer & Aging Institute.
WO, A, 9005142, May 1990, Imperial Cancer Research Technology Ltd.
WO, A, 8809344, Dec. 1988, Creative Biomolecules, Inc.
WO, A, 9107500, May 1991, (Unilever PLC).
WO, A, 9012319, Oct. 1990, John Muir Cancer & Aging Institute.
Nature, vol. 332, Mar. 1988, L. Reichmann et al: "Reshaping human antibodies for therapy", pp. 323–327.

* cited by examiner

Primary Examiner—Julie Burke
(74) Attorney, Agent, or Firm—Pillsbury Madison & Sutro LLP

(57) ABSTRACT

A reshaped human antibody or reshaped human antibody fragment having specificity for human polymorphic epithelial mucin (PEM) is produced by transferring the complementarity determining regions (CDRS) from a murine anti-HMFG hybridoma cell line HMFG1 into a human antibody variable region framework. The reshaped molecule can be used in the treatment or diagnosis of cancer.

21 Claims, 29 Drawing Sheets

Fig.1

MoVHHMFG1

```
                  5                   10                  15                  20
CAG GTT CAG CTG CAG CAG TCT GGA GCT GAG CTG ATG AAG CCT GGG GCC TCA GTG AAG ATA      60
Gln Val Gln Leu Gln Gln Ser Gly Ala Glu Leu Met Lys Pro Gly Ala Ser Val Lys Ile
              25                  30       CDR1      35                  40
TCC TGC AAG GCT ACT GGC TAC ACA TTC AGT GCC TAC TGG ATA GAG TGG GTA AAG CAG AGG     120
Ser Cys Lys Ala Thr Gly Tyr Thr Phe Ser Ala Tyr Trp Ile Glu Trp Val Lys Gln Arg
              45                  50  52  A                 55          CDR2
CCT GGA CAT GGC CTT GAG TGG ATT GGA GAG ATT TTA CCT GGA AGT AAT AAT TCT AGA TAC     180
Pro Gly His Gly Leu Glu Trp Ile Gly Glu Ile Leu Pro Gly Ser Asn Asn Ser Arg Tyr
          60                  65              70                  75
AAT GAG AAG TTC AAG GGC AAG GCC ACA TTC ACT GCT GAT ACA TCC TCC AAC ACA GCC TAC     240
Asn Glu Lys Phe Lys Gly Lys Ala Thr Phe Thr Ala Asp Thr Ser Ser Asn Thr Ala Tyr
      80  82  A   B   C           85                  90                  95
ATG CAA CTC AGC AGC CTG ACA TCT GAG GAC TCT GCG GTC TAT TAC TGT TCA AGG TCC TAC     300
Met Gln Leu Ser Ser Leu Thr Ser Glu Asp Ser Ala Val Tyr Tyr Cys Ser Arg Ser Tyr
CDR3   100  A                 105                 110
GAC TTT GCC TGG TTT GCT TAC TGG GGC CAA GGG ACT CCG GTC ACT GTC TCT GCA              354
Asp Phe Ala Trp Phe Ala Tyr Trp Gly Gln Gly Thr Pro Val Thr Val Ser Ala
```

Fig.2

MoVkHMFG1

```
                        5                        10                       15                        20
GAC ATT GTG ATG TCA CAG TCT CCA TCC CTA GCT GTG TCA GTT GGA GAG AAG GTT ACT        60
Asp Ile Val Met Ser Gln Ser Pro Ser Leu Ala Val Ser Val Gly Glu Lys Val Thr 25  27  A   B   C   D   E   F            30    CDR1
ATG AGC TGC AAG TCC AGT CAG AGC CTT TTA TAT AGT AGC AAT CAA AAG ATC TAC TTG GCC   120
Met Ser Cys Lys Ser Ser Gln Ser Leu Leu Tyr Ser Ser Asn Gln Lys Ile Tyr Leu Ala 35                        40                       45
TGG TAC CAG CAG AAA CCA GGG CAG TCT CCT AAA CTG CTG ATT TAC
Trp Tyr Gln Gln Lys Pro Gly Gln Ser Pro Lys Leu Leu Ile Tyr

CDR2
TGG GCA TCC ACT AGG                                                                180
Trp Ala Ser Thr Arg 55                        60                       65                        70
GAA TCT GGG GTC CCT GAT CGC TTC ACA GGC AGT GGA TCT GGG ACA GAT TTC ACT CTC ACC   240
Glu Ser Gly Val Pro Asp Arg Phe Thr Gly Ser Gly Ser Gly Thr Asp Phe Thr Leu Thr 75                        80                       85                        90
ATC AGC AGT GTG AAG GCT GAA GAC CTG GCA GTT TAT TAC TGT                            
Ile Ser Ser Val Lys Ala Glu Asp Leu Ala Val Tyr Tyr Cys

CDR3
CAG CAA TAT TAT AGA TAT                                                            300
Gln Gln Tyr Tyr Arg Tyr 95                        100                      105
CCT CGG ACG TTC GGT GGA GGC ACC AAG CTG GAA ATC AAA CGG                            342
Pro Arg Thr Phe Gly Gly Gly Thr Lys Leu Glu Ile Lys Arg
```

Fig. 3b1

FRAGMENT 1

```
         10         20         30         40         50         60
acagtagcag gcttgaggaa agcttctata tatgggtacc aatgacatcc actttgcctt
tgtcatcgtc cgaactcctt cgaagatat ataccatgg ttactgtagg tgaaacggaa 70         80         90        100        110        120
tctctccaca gGTGTCCACT CCCAGGTGCA GCTGGTGCAG TCTGGGGCAG AGGTGAAAAA
agagaggtgt cCACAGGTGA GGGTCCACGT CGACCACGTC AGACCCCGTC TCCACTTTTT 130        140        150        160        170        180
GCCTGGGGCC TCAGTGAAGG TCTCCTGCAA GGCTTCTGGC TACACCTTCA GTGCCTACTG
CGGACCCCGG AGTCACTTCC ACAGGACGTT CCGAAGACCG ATGTGGAAGT CACGGATGAC 190        200        210        220        230        240
GATAGAGTGG GTGCGCCAGG CTCCAGGAAA GGGCCTCGAG TGGGTCGGAT CCAGGGAGAT
CTATCTCACC CACGCGGTCC GAGGTCCTTT CCCGGAGCTC ACCCAGCCTA GGTCCCTCTA
```

Fig. 3b2

| OLIGONUCLEOTIDES CODE | LENGTH | 5' ←---- SEQUENCE ----→ 3' |
|---|---|---|
| VHHM1A | (32) | agc ttc tat ata tgg gta cca atg aca tcc ac |
| VHHM1B | (33) | ttt gcc ttt ctc aca ggT GTC CAC TCC CAG |
| VHHM1C | (36) | GTG CAG CTG GTG CAG TCT GGG GCA GAG GTG AAA AAG |
| VHHM1D | (33) | CCT GGG GCC TCA GTG AAG GTG TCC TGC AAG GCT |
| VHHM1E | (36) | TCT GGC TAC ACC TTC AGT GCC TAC TGG ATA GAG TGG |
| VHHM1F | (37) | GTG CGC CAG CGC CCT CCA GGA AAG GGC CTC GAG TGG GTC |
| VHHM1G | (40) | gag aaa ggc aaa gtg gat gtc att ggt acc cat ata tag a |
| VHHM1H | (36) | CTG CAC CAG CCC AGG CTT CAC CTG GAC ACc tgt gga |
| VHHM1I | (33) | TGA GGC CCC AGG AGC CTT TTT CAC CTG CCC AGA |
| VHHM1J | (33) | GGT GTA GCC AGA AGC CTT GCA GGA CAC CTT CAC |
| VHHM1K | (36) | AGC CTG GCG CAC CCA CTC GAG GCC CTT TCC TGG |
| VHHM1L | (29) | GAT CCG ACC GTA TCC GGC ACT GAA CCT GG |

Fig. 3b3

POSITIVE STRING:

VHHM1A : (21-52)
VHHM1B : (53-85)
VHHM1C : (86-121)
VHHM1D : (122-154)
VHHM1E : (155-190)
VHHM1F : (191-227)

NEGATIVE STRING:

VHHM1G : (25-64)
VHHM1H : (65-100)
VHHM1I : (101-133)
VHHM1J : (134-166)
VHHM1K : (167-202)
VHHM1L : (203-231)

Fig. 3cl

```
FRAGMENT 2
              10         20         30         40         50         60
     GACAGCCGTA GAGTGGGTGC AAGCTTCTCC AGGACTCGAG TGGGTCGGAG AGATTTTACC
     CTGTCGGCAT CTCACCCACG TTCGAAGAGG TCCTGAGCTC ACCCAGCCTC TCTAAAATGG 70         80         90        100        110        120
     TGGAAGTAAT AATTCTAGAT ACAATGAGAA GTTCAAGGGC CGAGTGACAG TCACTAGAGA
     ACCTTCATTA TTAAGATCTA TGTTACTCTT CAAGTTCCCG GCTCACTGTC AGTGATCTCT 130        140        150        160        170        180
     CACATCCACA AACACAGCCT ACATGGAGCT CAGCAGCCTG AGGATCCAGC AGCCTGAGGT
     GTGTAGGTGT TTGTGTCGGA TGTACCTCGA GTCGTCGGAC TCCTAGGTCG TCGGACTCCA
```

Fig. 3c2

| OLIGONUCLEOTIDES CODE | LENGTH | 5' ←—— SEQUENCE ——→ 3' |
|---|---|---|
| VHHM2A | (25) | AGC TTC TCC AGG ACT CGA GTG GGT C |
| VHHM2B | (27) | GGA GAG ATT TTA CCT GGA AGT AAT |
| VHHM2C | (39) | TCT AGA TAC AAT GAG AAG TTC AAG GGC CGA GTG AGA GTC |
| VHHM2D | (30) | ACT AGA GAC ACA TCC ACA AAC ACA GCC TAC |
| VHHM2E | (20) | ATG GAG CTC AGC AGC CTG AG |
| VHHM2F | (36) | AGG TAA AAT CTC TCC GAC CCA CTC GAG TCC TGG AGA |
| VHHM2G | (39) | GCC CTT GAA CTT CTC ATT GTA TCT AGA ATT ATT ACT TCC |
| VHHM2H | (24) | TGT GTC TCT AGT GAC TGT CAC TCG |
| VHHM2I | (42) | GAT CCT CAG GCT GCT GAG CTC CAT GTA GGC TGT GTT TGT GGA |

Fig. 3c3

POSITIVE STRING:
VHHM2A : (22-46)
VHHM2B : (47-73)
VHHM2C : (74-112)
VHHM2D : (113-142)
VHHM2E : (143-162)

NEGATIVE STRING:
VHHM2F : (26-61)
VHHM2G : (62-100)
VHHM2H : (101-124)
VHHM2I : (125-166)

Fig. 3dI

FRAGMENT 3

```
         10         20         30         40         50         60
CACATCCACA AGCTTAAACA CAGCCGAGCT CAGCAGCCTG AGGTCTGAGG ACACAGCCGT
GTGTAGGTGT TCGAATTTGT GTCGGCTCGA GTCGTCGGAC TCCAGACTCC TGTGTCGGCA 70         80         90        100        110        120
CTATTACTGT GCAAGATCCT ACGACTTTGC CTGGTTTGCT TACTGGGGCC AAGGGACTCT
GATAATGACA CGTTCTAGGA TGCTGAAACG GACCAAACGA ATGACCCCGG TTCCCTGAGA 130        140        150        160        170        180
GGTCACAGTC TCCTCAggtg agtccttaca acctctctct tctattcagt cgacatagat
CCAGTGTCAG AGGAGTccac tcaggaatgt tggagagaga agataagtca gctgtatcta 190
acgtggatcc
tgcacctagg
```

Fig. 3d2

| OLIGONUCLEOTIDES CODE | LENGTH | 5' ←—— SEQUENCE ——→ 3' |
|---|---|---|
| VHHM3A | (39) | AGC TTA AAC ACA GCC GAG CTC AGC AGC CTG AGG TCT GAG |
| VHHM3B | (27) | GAC ACA GCC GTC TAT TAC TGT GCA AGA |
| VHHM3C | (39) | TCC TAC GAC TTT GCC TGG TTT GCT TAC TGG GGC CAA GGG |
| VHHM3D | (39) | ACT CTG GTC ACA GTC TCC TCA ggt gag tcc tta caa cct |
| VHHM3E | (31) | ctc tct tct att cag tcg aca tag ata cgt g |
| VHHM3F | (17) | GAG CTC GGC TGT GTT TA |
| VHHM3G | (33) | ATA GAC GGC TGT GTC CTC AGA CCT CAG GCT GCT |
| VHHM3H | (39) | GTA AGC AAA CCA GGC AAA GTC GTA GGA TCT TGC ACA GTA |
| VHHM3I | (36) | acc TGA GGA GAC TGT GAC CAG AGT CCC TTG GCC CCA |
| VHMM3J | (29) | tga ata gaa gag aga ggt tgt aag gac tc |
| VHMM3K | (21) | gat cca cgt atc tat gtc gac |

Fig. 3d3

POSITIVE STRING:

VHHM3A : (11-49)
VHHM3B : (50-76)
VHHM3C : (77-115)
VHHM3D : (116-154)
VHHM3E : (155-185)

NEGATIVE STRING:

VHHM3F : (15-31)
VHHM3G : (32-64)
VHHM3H : (65-103)
VHHM3I : (104-139)
VHHM3J : (140-168)
VHHM3K : (169-189)

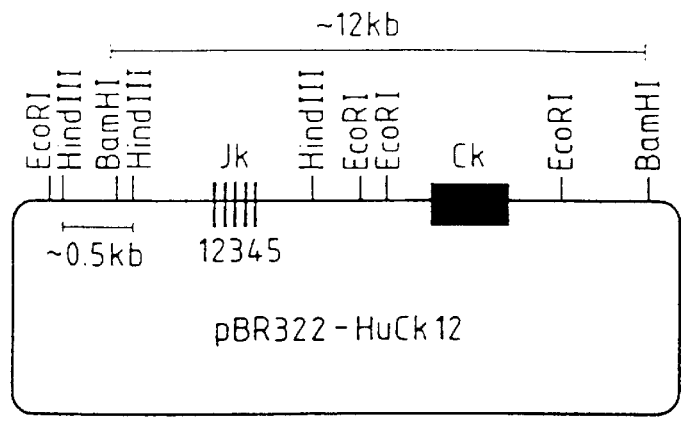
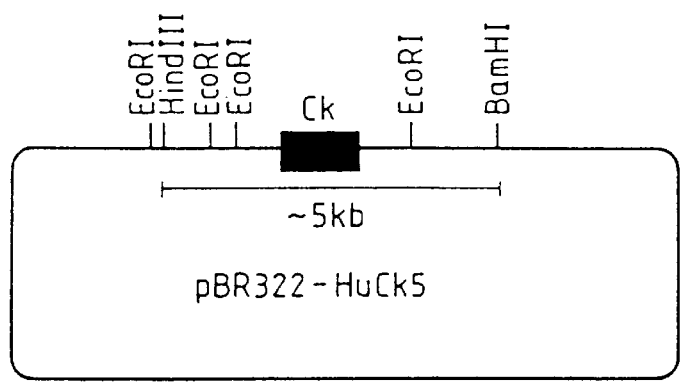
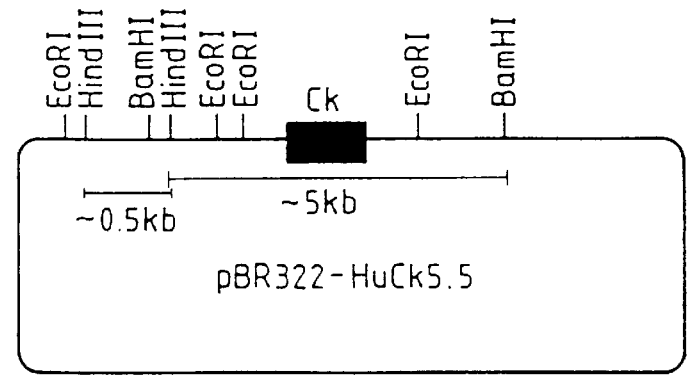
Fig. 8

Fig. 9

Oligonucleotides used for cloning variable region genes

I : mouse constant gamma1 primer

5' GAT AGA CAG ATG GGG GTG TCG TTT 3'

II : mouse constant kappa primer

5' AGA TGG ATA CAG TTG GTG CAG CAT 3'

Fig. 10

Oligonucleotides used to introduce KpnI and SalI in M13mp9HuVHLYS.

III : to introduce a KpnI in the HuVH leader intron

5' TGT CAT TGG TAC CCA TAT 3'

IV : to introduce a SalI 5' of the HuVHLYS gene

5' AAA TCT ATG TCG ACT GAA TAG 3'

Fig. 11

Oligonucleotides used for grafting of VkHMFG1 CDRs onto human kappa chain framework regions.

VI : VkHMFG1-CDR1

5' CTG CTG GTA CCA GGC CAA GTA GAT CTT TTG ATT GCT ACT ATA TAA AAG GCT CTG ACT GGA CTT ACA GGT GAT GGT 3'

VII : VkHMFG1-CDR2

5' GCT TGG CAC ACC AGA TTC CCT AGT GGA TGC CCA GTA GAT CAG CAG 3'

VIII : VkHMFG1-CDR3

5' CCC TTG GCC GAA CGT CCG AGG ATA TCT ATA ATA TTG CTG GCA GTA GGT 3'

Fig. 12

HuVHIconHMFG1

```
         5                  10                 15                 20
CAG GTG CAG CTG GTG CAG TCT GGG GCA GAG GTG AAA AAG CCT GGG GCC TCA GTG AAG GTG      60
Gln Val Gln Leu Val Gln Ser Gly Ala Glu Val Lys Lys Pro Gly Ala Ser Val Lys Val 25                 30          CDR1    35                   40
TCC TGC AAG GCT TCT GGC TAC ACC TTC AGT |GCC TAC TGG ATA GAG| TGG GTG CGC CAG GCT   120
Ser Cys Lys Ala Ser Gly Tyr Thr Phe Ser |Ala Tyr Trp Ile Glu| Trp Val Arg Gln Ala 45              50  52 A         CDR2                55
CCA GGA AAG GGC CTC GAG TGG GTC GGA |GAG ATT TTA CCT GGA AGT AAT AAT TCT AGA TAC   180
Pro Gly Lys Gly Leu Glu Trp Val Gly |Glu Ile Leu Pro Gly Ser Asn Asn Ser Arg Tyr 60                    65  A B C         70                 75
AAT GAG AAG TTC AAG GGC| CGA GTG ACA GTC ACT AGA GAC ACA GTC TCC ACA AAC ACA GCC TAC  240
Asn Glu Lys Phe Lys Gly| Arg Val Thr Val Thr Arg Asp Thr Val Ser Thr Asn Thr Ala Tyr 80   82 A B C             85                  90                        95
ATG GAG CTC AGC AGC CTG AGG TCT GAG GAC ACA GCC GTC TAT TAC TGT GCA AGA |TCC TAC   300
Met Glu Leu Ser Ser Leu Arg Ser Glu Asp Thr Ala Val Tyr Tyr Cys Ala Arg |Ser Tyr

CDR3  100 A                      105                 110
GAC TTT GCC TGG TTT GCT TAC| TGG GGC CAA GGG ACT CTG GTC ACA GTC TCC TCA            354
Asp Phe Ala Trp Phe Ala Tyr| Trp Gly Gln Gly Thr Leu Val Thr Val Ser Ser
```

Fig. 13

HuVkHMFG1

```
                  5                  10                 15                 20
GAC ATC CAG ATG ACC CAG AGC CCA AGC AGC CTG AGC GCC AGC GTG GGT GAC AGA GTG ACC     60
Asp Ile Gln Met Thr Gln Ser Pro Ser Ser Leu Ser Ala Ser Val Gly Asp Arg Val Thr
                 25   27   A                    30                              CDR1
ATC ACC TGT AAG TCC AGT CAG AGC CTT TTA TAT AGT AGC AAT CAA AAG ATC TAC TTG GCC    120
Ile Thr Cys Lys Ser Ser Gln Ser Leu Leu Tyr Ser Ser Asn Gln Lys Ile Tyr Leu Ala
         35                  40                  45                  50            CDR2
TGG TAC CAG CAG AAG CCA GGT AAG GCT CCA AAG CTG CTG ATC TAC TGG GCA TCC ACT AGG    180
Trp Tyr Gln Gln Lys Pro Gly Lys Ala Pro Lys Leu Leu Ile Tyr Trp Ala Ser Thr Arg
                 55                  60                  65                  70
GAA TCT GGT GTG CCA AGC AGA TTC AGC GGT AGC GGT AGC GGT ACC GAC TTC ACC TTC ACC    240
Glu Ser Gly Val Pro Ser Arg Phe Ser Gly Ser Gly Ser Gly Thr Asp Phe Thr Phe Thr
         75                  80                  85                             CDR3
ATC AGC AGC CTC CAG CCA GAG GAC ATC GCC ACC TAC TAC TGC CAG CAA TAT TAT AGA TAT    300
Ile Ser Ser Leu Gln Pro Glu Asp Ile Ala Thr Tyr Tyr Cys Gln Gln Tyr Tyr Arg Tyr
         95                  100                 105
CCT CGG ACG TTC GGC CAA GGG ACC AAG GTG GAA ATC AAA CGT                            342
Pro Arg Thr Phe Gly Gln Gly Thr Lys Val Glu Ile Lys Arg
```

SPECIFIC BINDING AGENTS

This invention relates to specific binding agents, and in particular to polypeptides containing amino acid sequences that bind specifically to other proteinaceous or non-proteinaceous materials. The invention most particularly concerns the production of such specific binding agents by genetic engineering.

Antibody structure

Natural antibody molecules consist of two identical heavy-chain and two identical light-chain polypeptides, which are covalently linked by disulphide bonds. FIG. 14 of the accompanying drawings diagramatically represents the typical structure of an antibody of the IgG class. Each of the chains is folded into several discrete domains. The N-terminal domains of all the chains are variable in sequence and therefore called the variable regions (V-regions). The V-regions of one heavy (VH) and one light chain (VL) associate to form the antigen-binding site. The module formed by the combined VH and VL domains is referred to as the Fv (variable fragment) of the antibody. The C-terminal ends of both heavy and light chains are more conserved in sequence and therefore referred to as the constant regions. Heavy chain constant regions are composed of several domains, eg. the heavy chain constant region of the gamma-isotype (IgG) consists of three domains (CH1, CH2, CH3) and a hinge region which connects the CH1 and CH2 domains. The hinges of the two heavy chains are covalently linked together by disulphide bridges. Light chains have one constant domain which packs against the CH1 domain. The constant regions of the antibody molecule are involved in effector functions such as complement lysis and clearing by Antibody Dependant Cell Cytotoxicity (ADCC). Classical digestion of an antibody with the protease papain yields three fragments. One fragment contains the CH2 and CH3 domains and, as it crystallises easily, was called the Fc fragment. The other two fragments were designated the Fab (antigen-binding) fragments, they are identical and contain the entire light chain combined with the VH and CH1 domain. When using pepsin, the proteolytic cleavage is such that the two Fabs remain connected via the hinge and form the (Fab)$_2$ fragment. Each of the domains is represented by a separate exon at the genetic level.

The variable regions themselves each contain 3 clusters of hypervariable residues, in a framework of more conserved sequences. These hypervariable regions interact with the antigen, and are called the Complementarity Determining Regions (CDRs). The more conserved sequences are called the Framework Regions (FRs). See Kabat et al (1987). X-ray studies of antibodies have shown that the CDRs form loops which protrude from the top of the molecule, whilst the FRs provide a structural beta-sheet framework.

Modified antibodies

In one embodiment, the invention relates to so-called "reshaped" or "altered" human antibodies, ie. immunoglobulins having-essentially human constant and framework regions but in which the complementarity determining regions (CDRs) correspond to those found in a non-human immunoglobulin, and also to corresponding reshaped antibody fragments.

The general principles by which such reshaped human antibodies and fragments may be produced are now well-known, and reference can be made to Jones et al (1986), Riechmann et al (1988), Verhoeyen et al (1988), and EP-A-239400 (Winter). A comprehensive list of relevant literature references is provided later in this specification.

Reshaped human antibodies and fragments have particular utility in the in-vivo diagnosis and treatment of human ailments because the essentially human proteins are less likely to induce undesirable adverse reactions when they are administered to a human patient, and the desired specificity conferred by the CDRs can be raised in a host animal, such as a mouse, from which antibodies of selected specificity can be obtained more readily. The variable region genes can be cloned from the non-human antibody, and the CDRs grafted into a human variable-region framework by genetic engineering techniques to provide the reshaped human antibody or fragment. To achieve this desirable result, it is necessary to identify and sequence at least the CDRs in the selected non-human antibody, and preferably the whole non-human variable region sequence, to allow identification of potentially important CDR-framework interactions.

Antibodies raised against the human milk fat globule (HMFG), generally in a delipidated state, can exhibit a broad spectrum of reactivity with epithelial origin neoplasms, particularly carcinomas of the breast, ovary, uterus and lung. See Taylor-Papadimitriou et al (1981) and Arklie et al (1981). One well-characterised antibody (designated HMFG1) is known to bind to a component of the HMFG, also found in some body tissues, some cancer tissues and urine, which has been designated polymorphic epithelial mucin (PEM) (Gendler et al, 1988). Binding is thought to involve the peptide core of the PEM. Corresponding useful specificity can be achieved by raising antibodies against cancer cells, for example breast cancer cell lines.

EP-A2-0369816 (The University of Melbourne, Xing et al) describes monoclonal antibodies specific for human polymorphic epithelial mucin, which bind to a defined amino acid sequence. It is suggested in EP-A2-0369816 that the described antibodies may be "humanised" according to the method of Riechmann et al (1988). However, Xing et al do not describe the actual preparation of any such reshaped anti-PEM antibodies.

SUMMARY OF THE INVENTION

The invention provides, as one embodiment, a synthetic specific binding polypeptide having specificity for a polymorphic epithelial mucin (PEM), and especially a synthetic specific binding polypeptide having anti-human milk fat globule (HMFG) specificity, containing one or more of the CDRs depicted in FIGS. 1 and 2 of the accompanying drawings. By synthetic, we particularly mean that the polypeptide is produced by recombinant DNA technology, and to that extent at least is different from a naturally-occurring or naturally-induced specific binding agent having identical specificity. Alternatively, the synthetic polypeptide has been produced by artificially assembling a sequence of amino acids to produce a novel or nature-identical molecule. The synthetic polypeptide can be equivalent to an intact conventional antibody, or equivalent to a multiple or. single-chain fragment of such an antibody, or can be simply a material that includes one or more sequences that confer the desired specific binding capability.

The invention provides as an important embodiment a reshaped human antibody, or a reshaped human antibody fragment, having anti-PEM specificity, and especially having anti-HMFG specificity, containing one or more of the CDRs depicted in FIGS. 1 and 2 of the accompanying drawings. Preferably, the reshaped antibody or fragment of the invention contains all 3 of the CDRs depicted in FIG. 1 of the accompanying drawings, in a human heavy chain variable region framework. Alternatively, or in addition, the reshaped antibody or fragment of the invention contains all 3 of the CDRs depicted in FIG. 2 of the accompanying drawings, in a human light chain variable region framework.

Another embodiment of the invention is a reshaped antibody or reshaped antibody fragment containing a protein sequence as depicted in FIG. 12 and/or FIG. 13 of the accompanying drawings.

Other important embodiments of the invention are an expression vector incorporating a DNA sequence as depicted in FIG. 12 and/or FIG. 13 of the accompanying drawings, and an expression vector incorporating a DNA sequence encoding one or more of the protein sequences designated as being a CDR in FIG. 1 and/or FIG. 2 of the accompanying drawings.

An important aspect of the invention is a stable host cell line containing a foreign gene that causes the host cell line to produce a specific binding agent according to the invention. This can be a stable host cell line containing a foreign gene that encodes at least one of the amino acid sequences designated as being a CDR in FIG. 1 and/or FIG. 2 of the accompanying drawings, together with a protein framework that enables the encoded amino acid sequence when expressed to function as a CDR having specificity for HMFG.

The invention also provides an immortalised mammalian cell line, or a yeast, or other eukaryotic cell, or a prokaryotic cell such as a bacterium, producing a reshaped antibody or fragment according to the invention.

Another important aspect of the invention is a synthetic specific binding agent, reshaped human antibody or reshaped human antibody fragment, having specificity equivalent to that of the gamma-1, kappa anti-HMFG monoclonal antibody "HMFG1".

The invention also provides two novel plasmids, pSVgpt-HuVHHMFG1-HuIgG1 and pSVneo-HuVkHMFG1-HuCk, and these plasmids can be used in the production of a synthetic specific binding agent, reshaped human antibody or reshaped human antibody fragment.

These plasmids are contained in novel *E. coli* strains NCTC 12411 and NCTC 12412, respectively.

Other aspects of the invention are:
a) A DNA sequence encoding a reshaped human antibody heavy-chain variable region having specificity for HMFG, as contained in *E. coli* NCTC 12411.
b) A DNA sequence encoding a reshaped human antibody light-chain variable region having specificity for HMFG, as contained in *E. coli* NCTC 12412.
c) A reshaped human antibody heavy-chain variable region having specificity for HMFG, producible by means of the expression vector contained in *E. coli* NCTC 12411.
d) A reshaped human antibody light-chain variable region having specificity for HMFG, producible by means of the expression vector contained in *E. coli* NCTC 12412.
e) A reshaped human antibody or reshaped human antibody fragment, comprising at least one variable region according to c) or d) above.

A particular embodiment of the invention is therefore a reshaped human antibody or reshaped human antibody fragment possessing anti-HMFG specificity and incorporating a combination of CDRs (which may, for example, be cloned from a murine anti-HMFG immunoglobulin) having the amino acid sequences identified as CDR1, CDR2 and CDR3 respectively in FIGS. 1 and 2 of the accompanying drawings, which respectively represent the heavy chain variable region (VH) and light chain variable region (Vk) of a murine anti-HMFG monoclonal antibody that we have cloned and sequenced. In the case of an intact antibody, or a fragment comprising at least one heavy chain variable region and at least one light chain variable region, the reshaped antibody or fragment preferably contains all six CDRs from the non-human source. To be most effective in binding, the CDRs should preferably be sited relative to one another in the same arrangement as occurs in the original non-human antibody, e.g. the VH CDRs should be in a human VH framework, and in the order in which they occur naturally in the non-human antibody.

As will be apparent to those skilled in the art, the CDR sequences and the surrounding framework sequences can be subject to modifications and variations without the essential specific binding capability being significantly reduced. Such modifications and variations can be present either at the genetic level or in the amino acid sequence, or both. Accordingly, the invention encompasses synthetic (reshaped) antibodies and fragments that are functionally equivalent to those described herein having precisely defined genetic or amino acid sequences.

The invention can also be applied in the production of bi-specific antibodies, having two Fab portions of different specificity, wherein one of the specificities is conferred by a reshaped human variable chain region incorporating one or more of the CDRs depicted in FIGS. 1 and 2 of the accompanying drawings.

The invention can also be applied in the production of so-called single-chain antibodies (for example, as disclosed in Genex EP-A-281604), and also to polysaccharide-linked antibodies (see Hybritech EP-A-315456), and other modified antibodies.

Any human constant regions (for example, gamma 1, 2, 3 or 4-type) can be used.

Antibody fragments retaining useful specific binding properties can be (Fab)$_2$, Fab, Fv, VH or Vk fragments. These can be derived from an intact reshaped antibody, for example by protease digestion, or produced as such by genetic engineering.

Practical applications of the invention

An important aspect of the invention is a reshaped human anti-HMFG antibody or fragment, as defined above, linked to or incorporating an agent capable of retarding or terminating the growth of cancerous cells, or to an imaging agent capable of being detected while inside the human body. The invention also includes injectable compositions comprising either of such combinations in a pharmaceutically acceptable carrier, such as saline solution, plasma extender or liposomes. The invention also includes the use, in a method of human cancer therapy or imaging, of a reshaped human anti-HMFG antibody or fragment as defined above. The invention further includes the use of such an antibody or fragment for the manufacture of a medicament for therapeutic application in the relief of cancer in humans, or the use of such an antibody or fragment in the manufacture of a diagnostic composition for in-vivo diagnostic application in humans.

The Fc region of the antibody, itself using pathways and mechanisms available in the body, such as complement lysis and antibody dependent cellular cytotoxicity, can be used to affect adversely the growth of cancerous cells. In this embodiment, no additional reagent need be linked to the reshaped antibody.

Examples of agents capable of affecting adversely the growth of cancerous cells include radioisotopes, such as Yttrium 90 and Iodine 131; drugs such as methotrexate; toxins such as ricin or parts thereof; and enzymes which may for example turn an inactive drug into an active drug at the site of antibody binding.

Examples of imaging agents include radioisotopes generating gamma rays, such as Indium 111 and Technetium 99;

radioisotopes generating positrons, such as Copper 64; and passive agents such as Barium which act as contrast agents for X-rays, and Gadolinium in nmr/esr scanning.

In order to link a metallic agent, such as a radioisotope, to a specific binding agent of the invention, it may be necessary to employ a coupling or chelating agent. Many suitable chelating agents have been developed, and reference can be made for example to U.S. Pat. No. 4,824,986, U.S. Pat. No. 4,831,175, U.S. Pat. No. 4,923,985 and U.S. Pat. No. 4,622,420. Techniques involving the use of chelating agents are described, for example, in U.S. Pat. No. 4,454,106, U.S. Pat. No. 4,722,892, Moi et al (1988), McCall et al (1990), Deshpande et al (1990) and Meares et al (1990).

The use of radiolabelled antibodies and fragments in cancer imaging and therapy in humans is described for example in EP 35265. It may be advantageous to use the radiolabelled cancer-specific antibody or fragment in conjunction with a non-specific agent radiolabelled with a different isotope, to provide a contrasting background for so-called subtraction imaging.

The antibody reagents of the invention can be used to identify, e.g. by serum testing or imaging, and/or to treat, PEM-producing cancers. Such cancers can occur as for example, carcinomas of breast, ovary, uterus and lung, or can manifest themselves as liquids such as pleural effusions.

Modified antibody production

The portions of the VH and VL regions that by convention (Kabat, 1987) are designated as being the CDRs may not be the sole features that need to be transferred from the non-human monoclonal antibody. Sometimes, enhanced antibody performance, in terms of specificity and/or affinity, can be obtained in the reshaped human antibody if certain non-human framework sequences are conserved in the reshaped human antibody.- The objective is to conserve the important three-dimensional protein structure associated with the CDRs, which is supported by contacts with framework residues.

The normal starting point from which a reshaped antibody in accordance with the invention can be prepared, is a cell (preferably an immortalised cell line), derived from a non-human host animal (for example, a mouse), which expresses an antibody having specificity against HMFG or PEM. Such a cell line can, for example, be a hybridoma cell line prepared by conventional monoclonal antibody technology. Preferably, the expressed antibody has a high affinity and high specificity for HMFG, because it should be anticipated that some loss of affinity and/or specificity may occur during the transfer of these properties to a human antibody or fragment by the procedures of the invention. By selecting a high specificity antibody as the parent antibody, the likelihood that the final reshaped antibody or fragment will also exhibit effective binding properties is enhanced.

The next stage is the cloning of the cDNA from the cell expressing the selected non-human antibody, and sequencing and identification of the variable region genes including the sequences encoding the CDRS. The experimental procedures involved can now be regarded as routine in the art, although they are still laborious.

If the object is to produce a reshaped complete human antibody, or at least a fragment of such an antibody which will contain both heavy and light variable domains, it will be necessary to sequence the cDNA associated with both of these domains.

Once the relevant cDNA sequence or sequences have been analysed, it is necessary to prepare one or more replicable expression vectors containing a DNA sequence which encodes at least a variable domain of an antibody, which variable domain comprises human framework regions together with one or more CDRs derived from the selected non-human anti-HMFG antibody. The DNA sequence in each vector should include appropriate regulatory sequences necessary to ensure efficient transcription and translation of the gene, particularly a promoter and leader sequence operably linked to the variable domain sequence. In a typical procedure to produce a reshaped antibody or fragment in accordance with the invention, it may be necessary to produce two such expression vectors, one containing a DNA sequence for a reshaped human light chain and the other, a DNA sequence for a reshaped human heavy chain. The expression vectors should be capable of transforming a chosen cell line in which the production of the reshaped antibody or fragment will occur. Such a cell line may be for example, a stable non-producing myeloma cell line, examples (such as NSO and sp2-0) of which are readily available commercially. An alternative is to use a bacterial system, such as *E. coli*, as the expression vehicle for the reshaped antibody or fragment. The final stages of the procedure therefore involve transforming the chosen cell line or organism using the expression vector or vectors, and thereafter culturing the transformed cell line or organism to yield the reshaped human antibody or fragment.

By way of example only, detailed steps by means of which appropriate expression vectors can be prepared are given later in this specification. The manipulation of DNA material in a suitably equipped laboratory is now a well-developed art, and the procedures required are well within the skill of those versed in this art. :Many appropriate genomic and cDNA libraries, plasmids, restriction enzymes, and the various reagents and media which are required in order to perform such manipulations, are available commercially from suppliers of laboratory materials. For example, genomic and cDNA libraries can be purchased from Clontech Laboratories Inc. The steps given by way of example below are purely for the guidance of the reader of this specification, and the invention is in no way critically dependent upon the availability of one or more special starting materials. In practice, the skilled person has a wide range of materials from which to choose, and can exploit and adapt the published technology using acquired experience and materials that are most readily available in the scientific environment. For example, many plasmids fall into this category, having been so widely used and circulated within the relevant scientific community that they can now be regarded as common-place materials.

EXAMPLES

The procedure used to prepare reshaped anti-HMFG human antibodies is described in detail below, by way of example only, with reference to the accompanying drawings, of which:

FIG. 1 shows the cDNA sequence (SEQ ID NO:13) coding for a murine heavy chain variable region having anti-HMFG specificity. The 3 classical CDRs are indicated, together with an amino acid sequence (SEQ ID NO:14) matching the cDNA code.

FIG. 2 shows the cDNA sequence (SEQ ID NO:15 and SEQ ID NO:16) coding for a murine light chain variable region having anti-HMFG specificity.

Figure 3A:
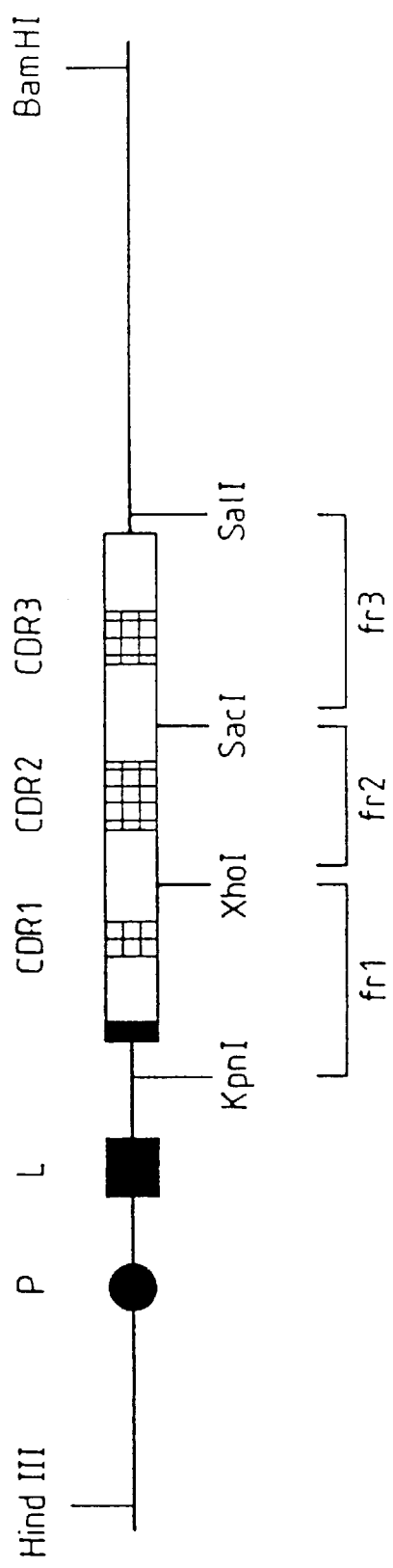
FIG. 3a shows a design for a synthesic reshaped human VH gene with HMFG1 specificity (HuVHIconHMFG1 gene cassette) containing 3 fragments.

FIGS. 3b1 to 3d3 show the sequence of the respective fragments in FIG. 3a, and also the oligonucleotides used in the assembly of each fragment (SEQ ID NO:17–SEQ ID NO:51).

FIGS. 4a, 4b, 4c and 4d together show a route by which an expression vector encoding a reshaped human heavy chain incorporating the CDRs of FIG. 1, can be prepared.

Figure 5A:
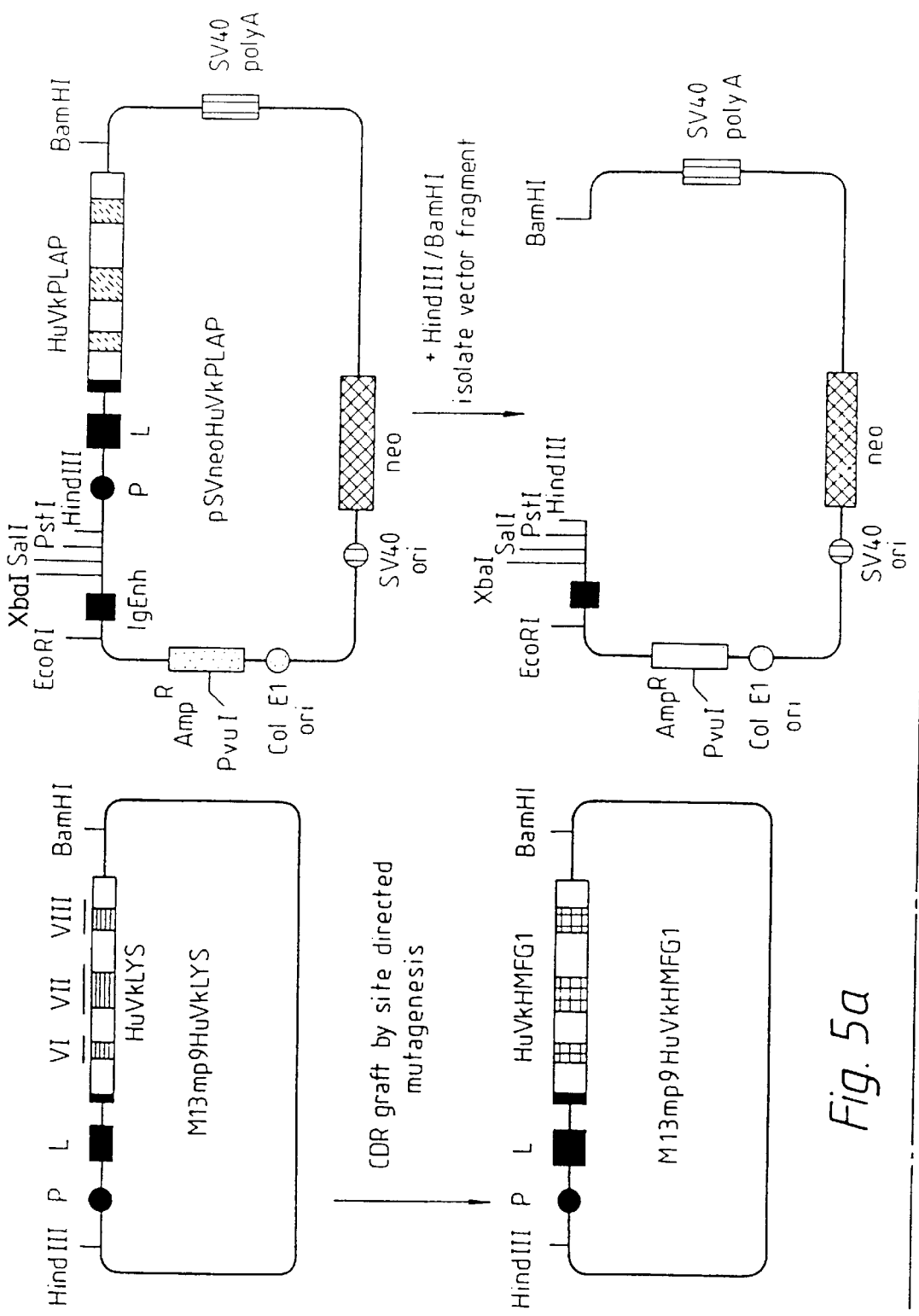
Figure 5A:
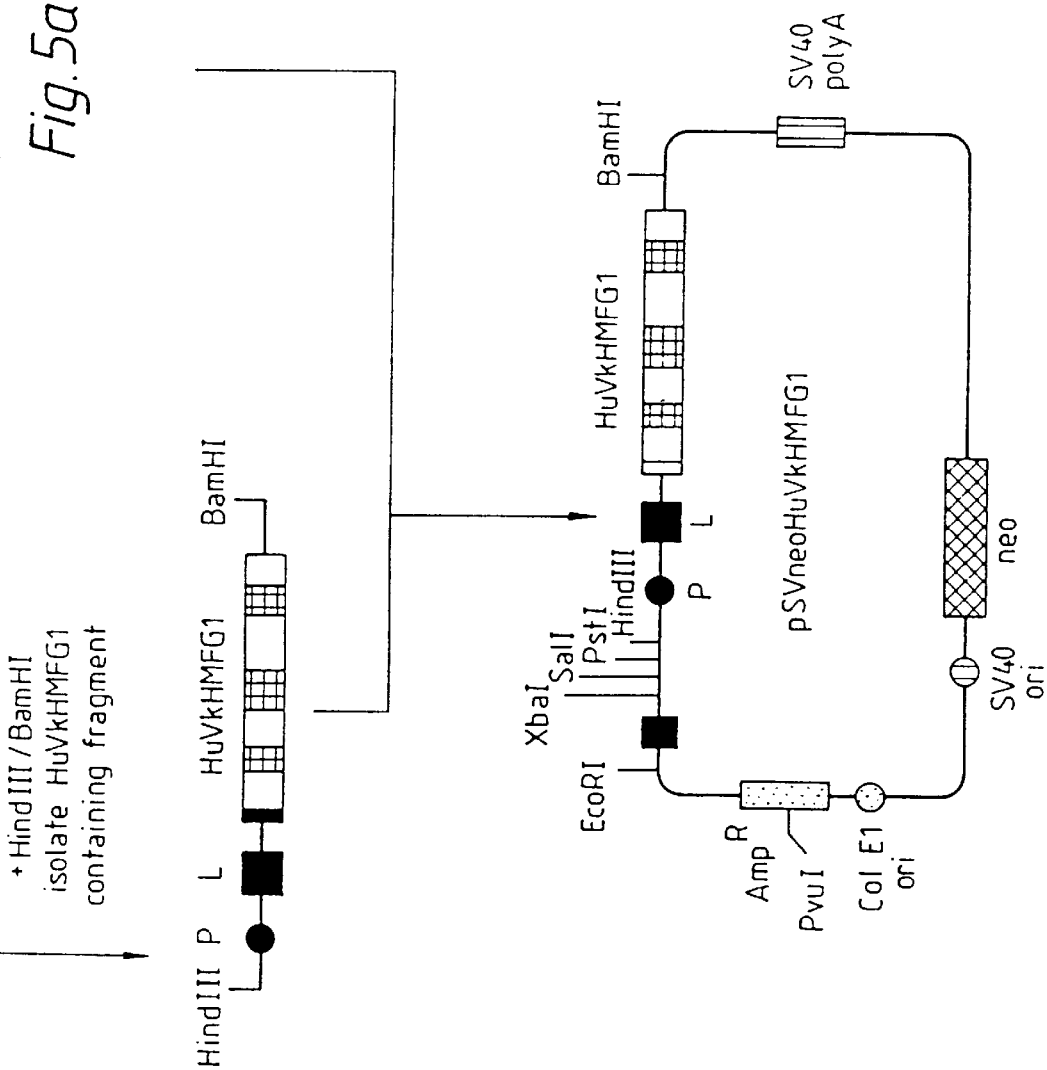
Figure 5B:
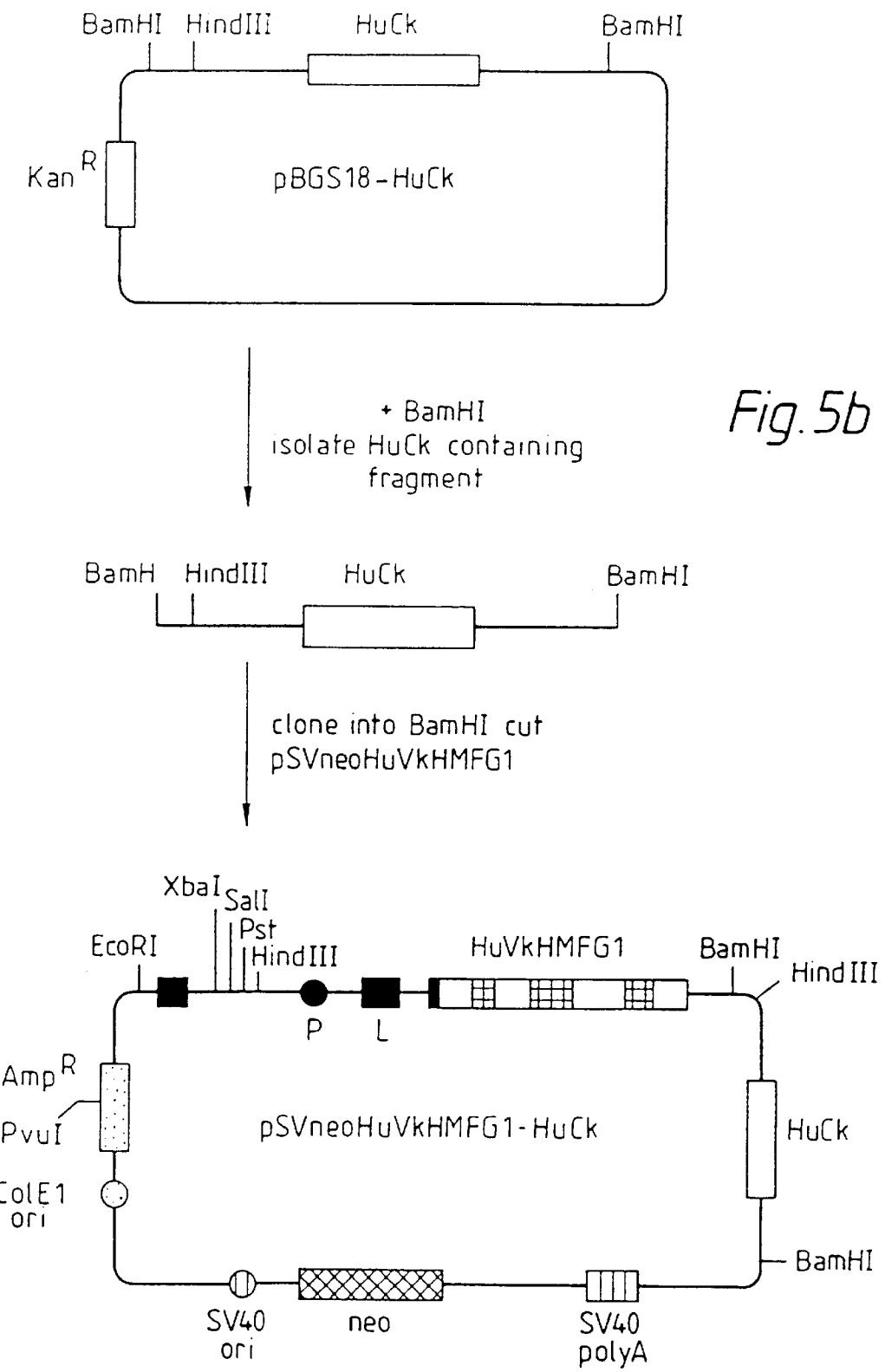

FIGS. 5a and 5b together show a similar transformation route to obtain an expression vector encoding a reshaped human light chain incorporating the CDRs of FIG. 2, can be prepared.

Figure 6:
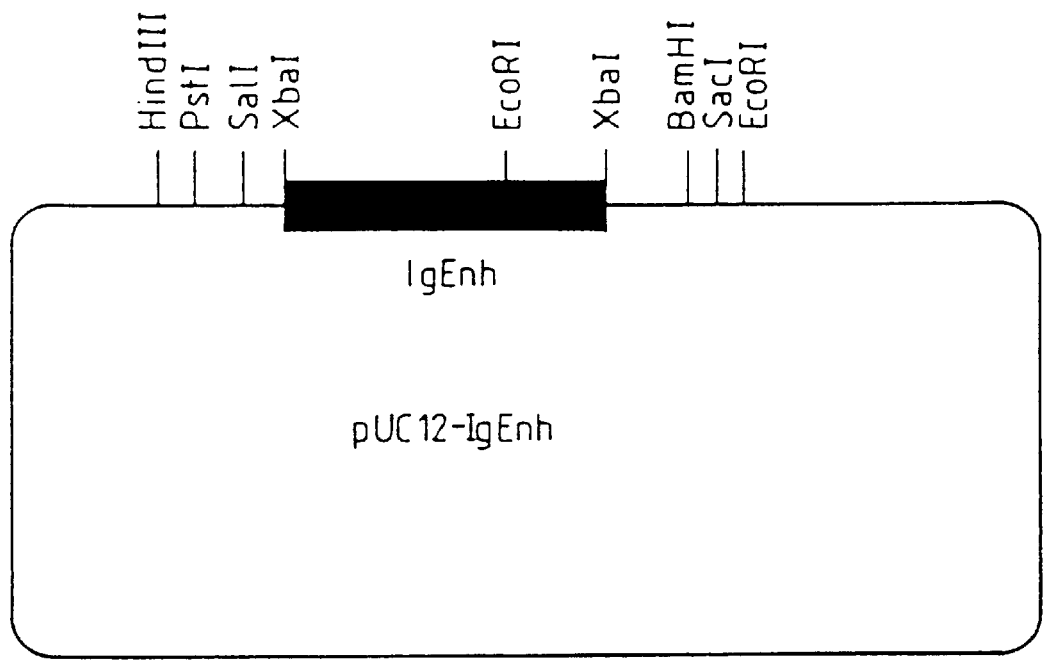

FIG. 6 shows the plasmid pUC12-IgEnh, which contains an enhancer sequence used in the routes of FIGS. 4a to 5b.

Figure 4A:
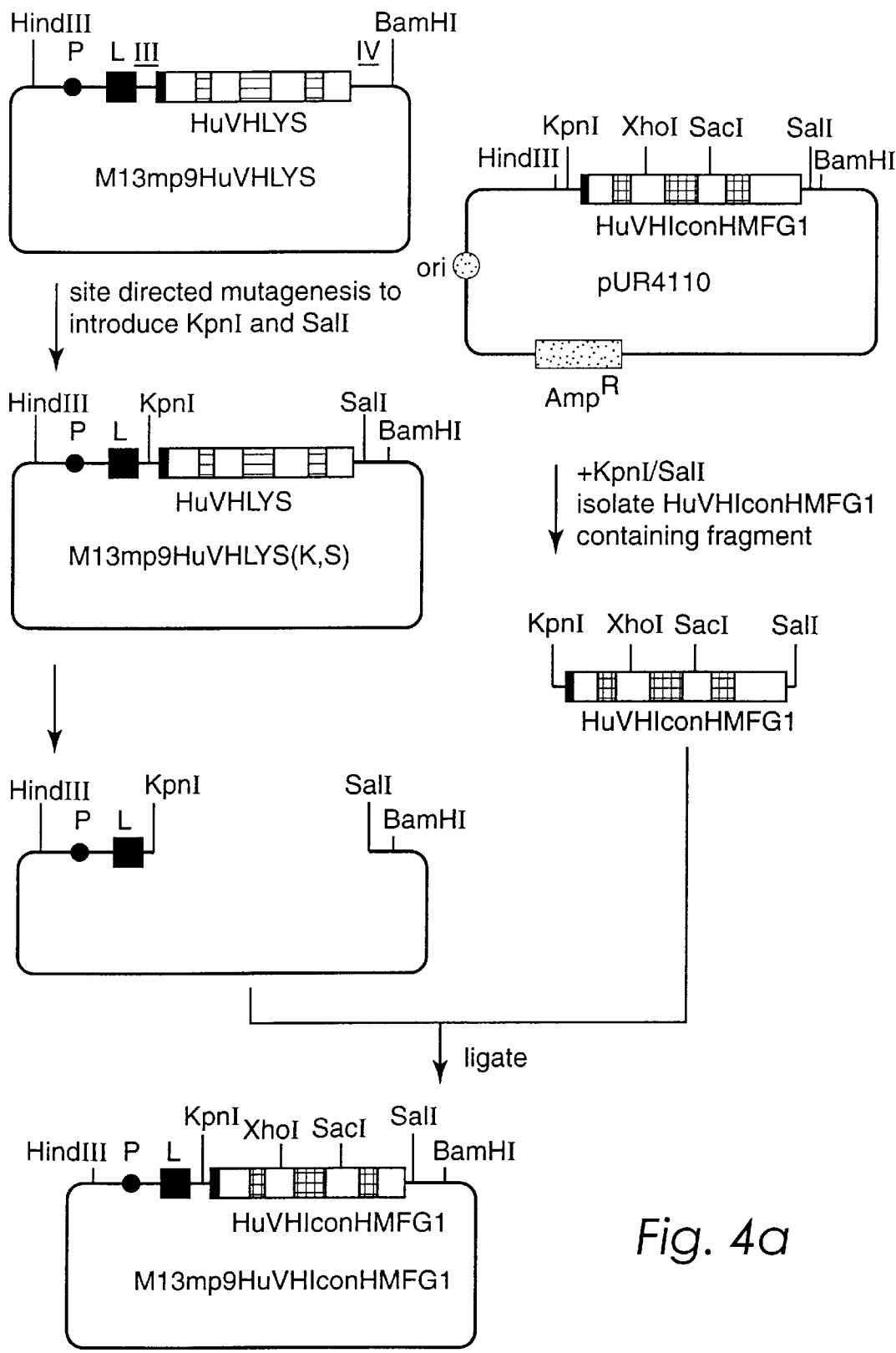
Figure 4B:
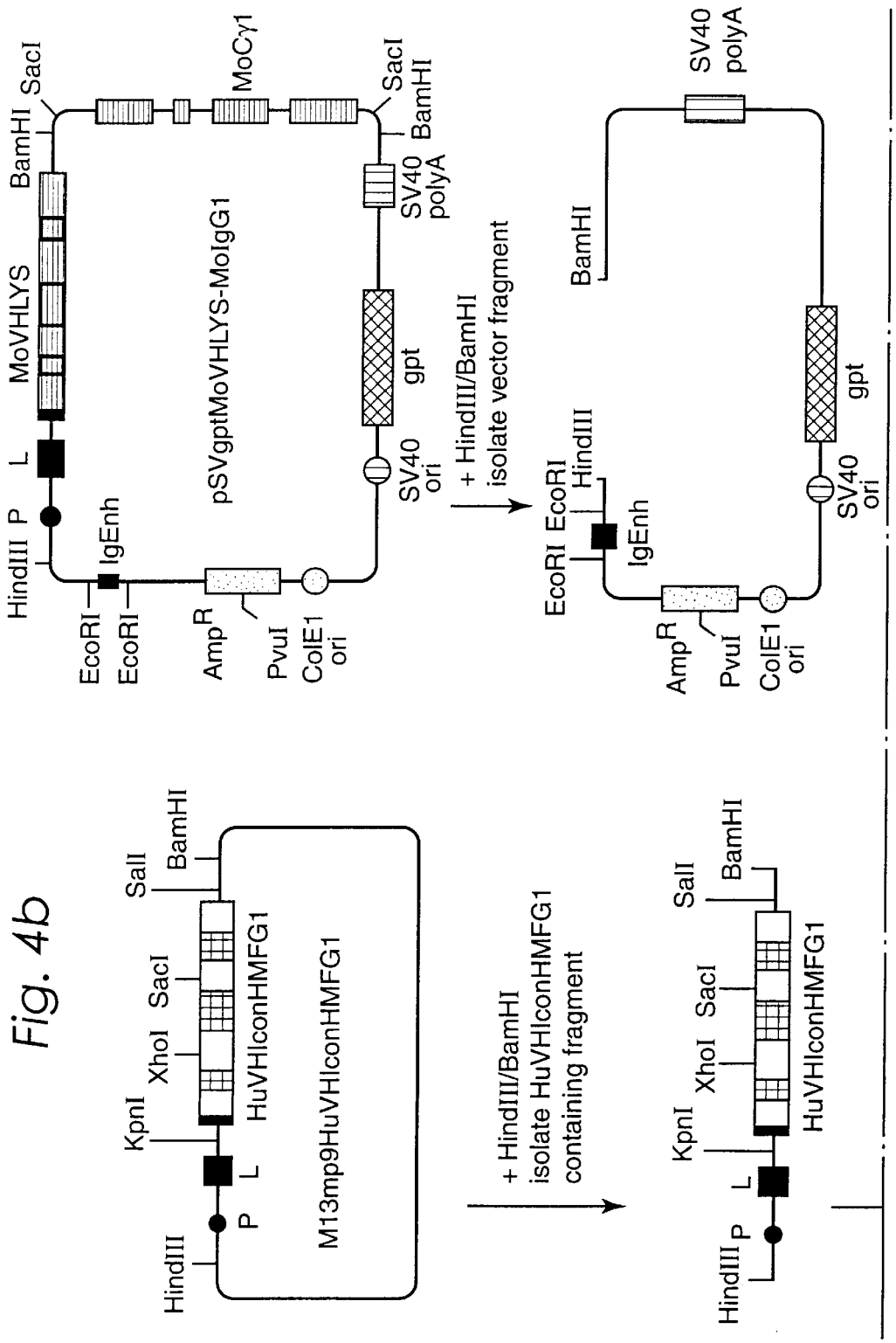
Figure 4C:
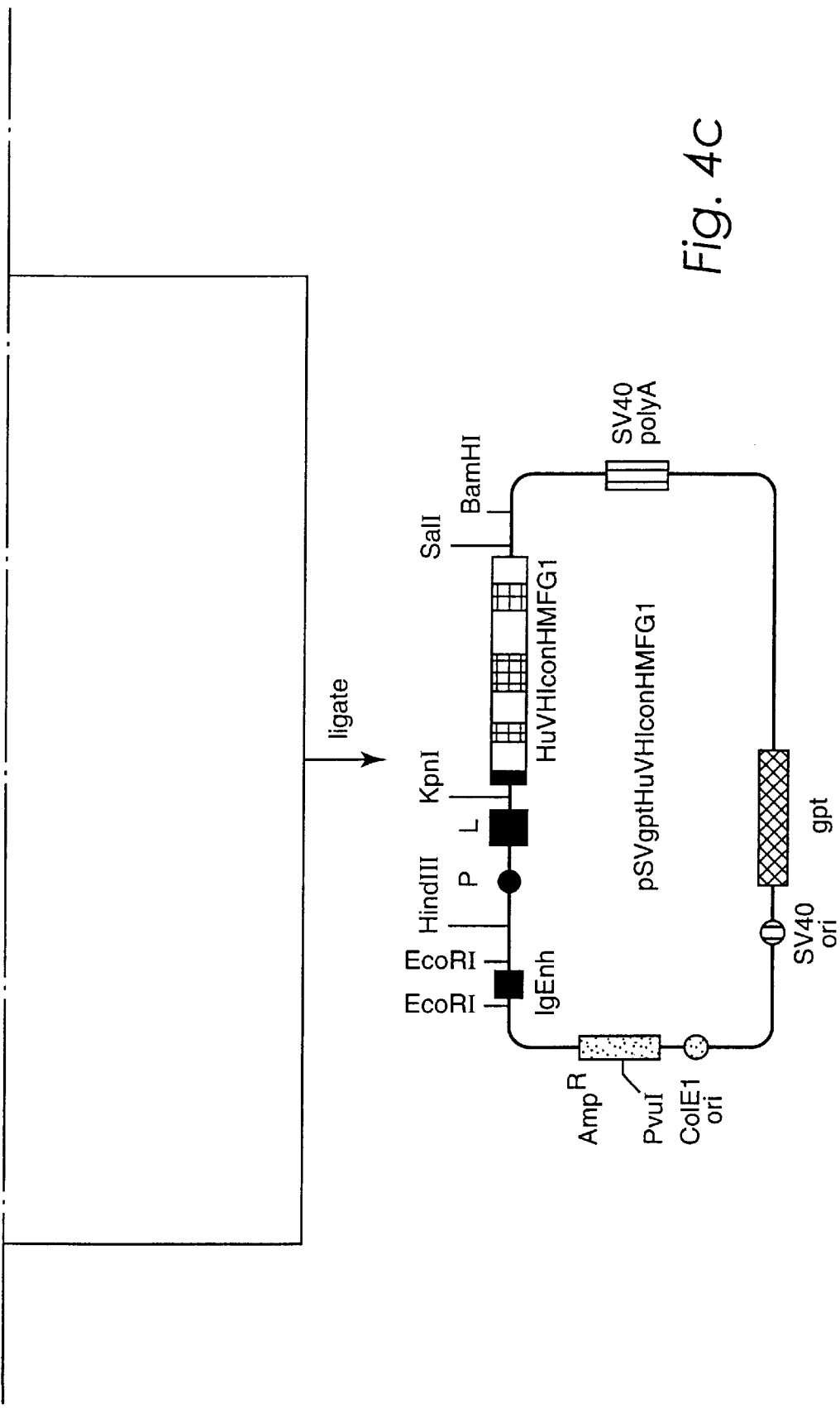
Figure 4D:
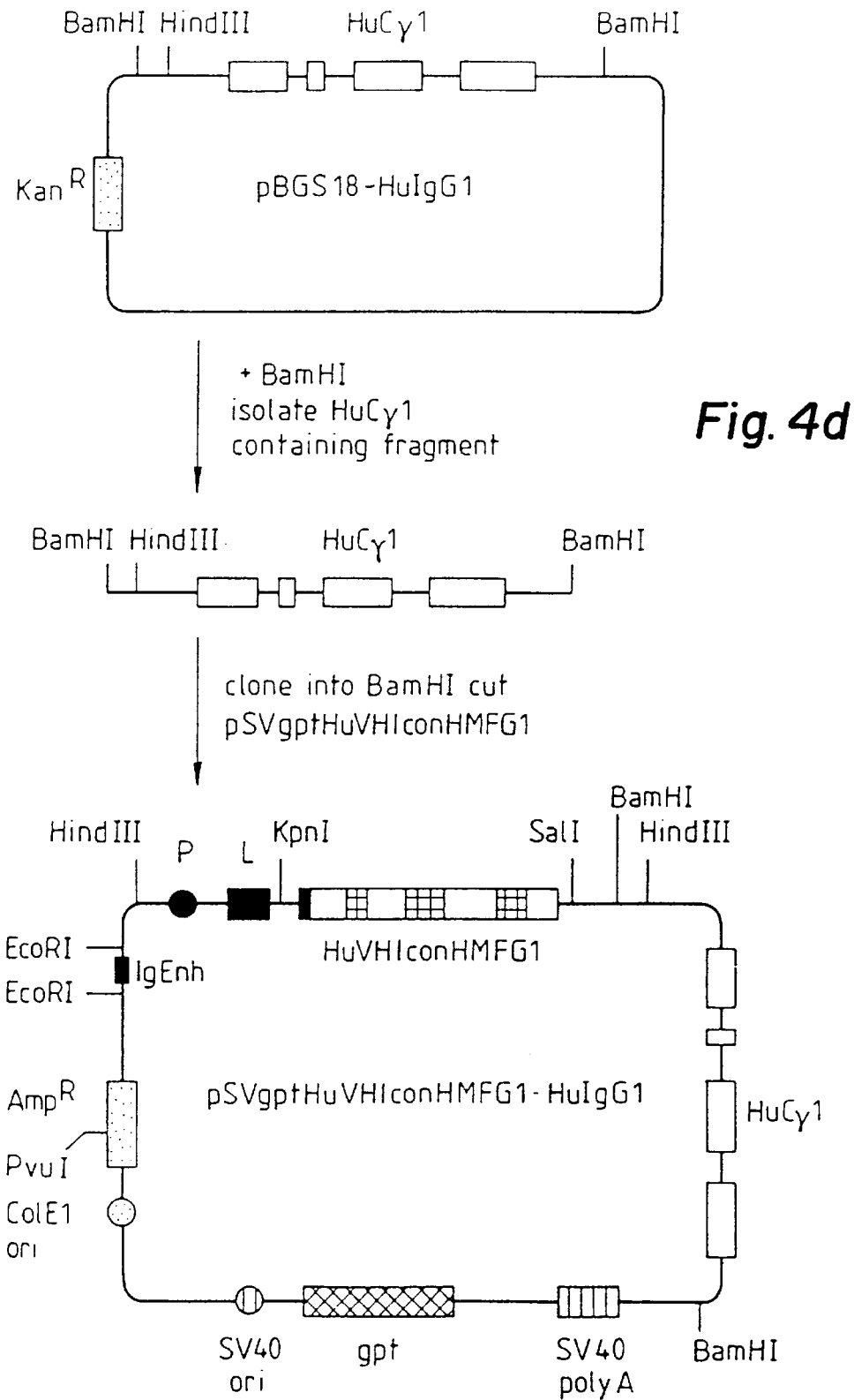
Figure 7:
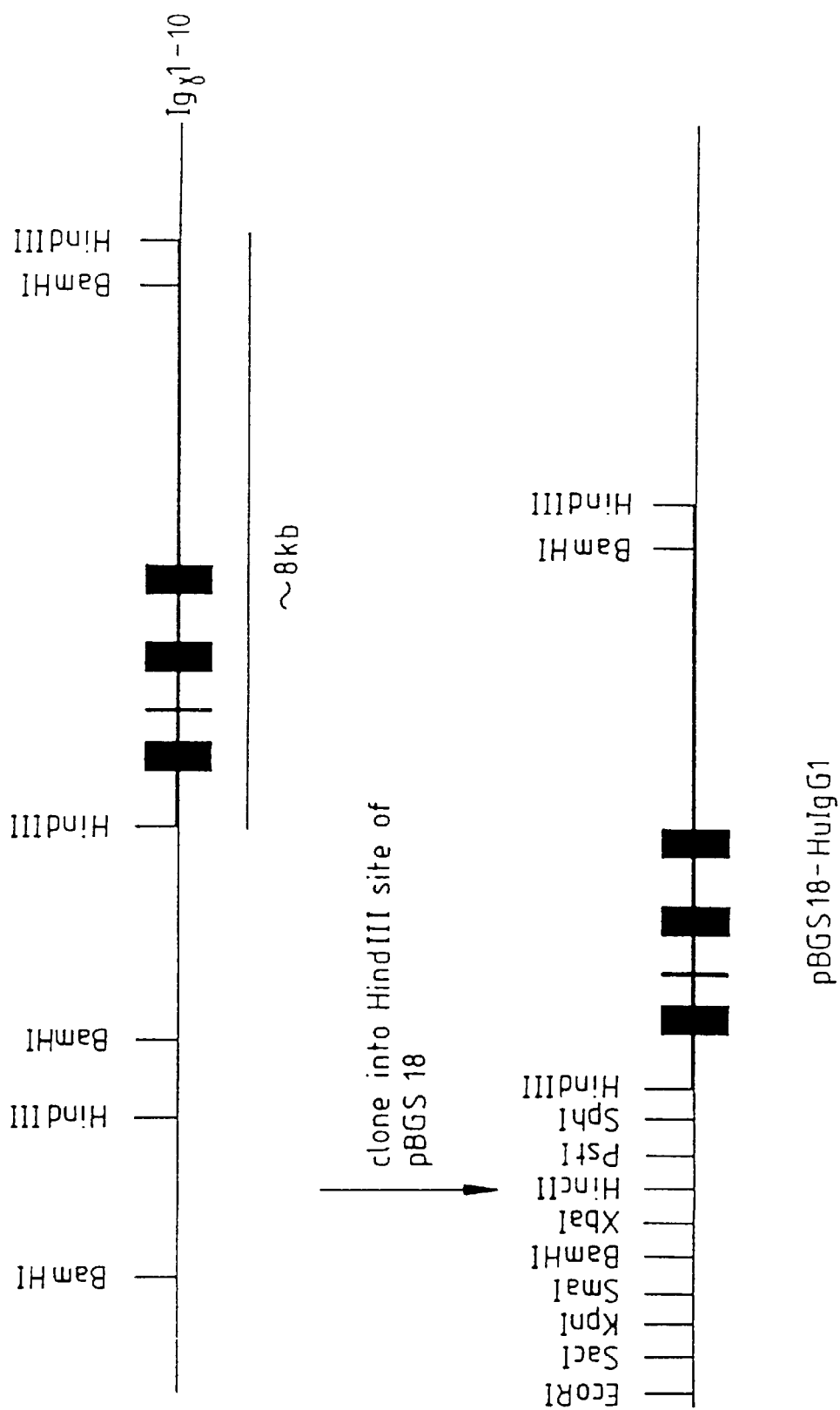

FIG. 7 shows the source of plasmid pBGS18-HuIgG1 used in the route of FIG. 4d.

FIG. 8 shows the source of plasmid pBGS18-HuCk used in the route of FIG. 5b.

FIG. 9 shows two synthetic oligonucleotide sequences I and II (SEQ ID NO:52 and SEQ ID NO:53) used in cloning the cDNA sequences of FIGS. 1 and 2.

FIG. 10 shows two synthetic oligonucleotide sequences III and IV (SEQ ID NO:54 and SEQ ID NO:55) used to introduce the Kpn I and Sal I restriction sites:in M13mp9HuVHLYS respectively, in the route depicted in FIG. 4a.

FIG. 11 shows three synthetic oligonucleotide sequences VI, VII and VIII (SEQ ID NO:56 and SEQ ID NO:57 and SEQ ID NO:58) used to graft the Vk HMFG1 CDRs onto the human VK REI framework regions in the route depicted in FIG. 5a.

FIGS. 12 and 13 show the cDNA and amino acid sequences of the resulting reshaped human heavy and light chain variable regions respectively (SEQ ID NO:59 through SEQ ID NO:62).

Figure 14:
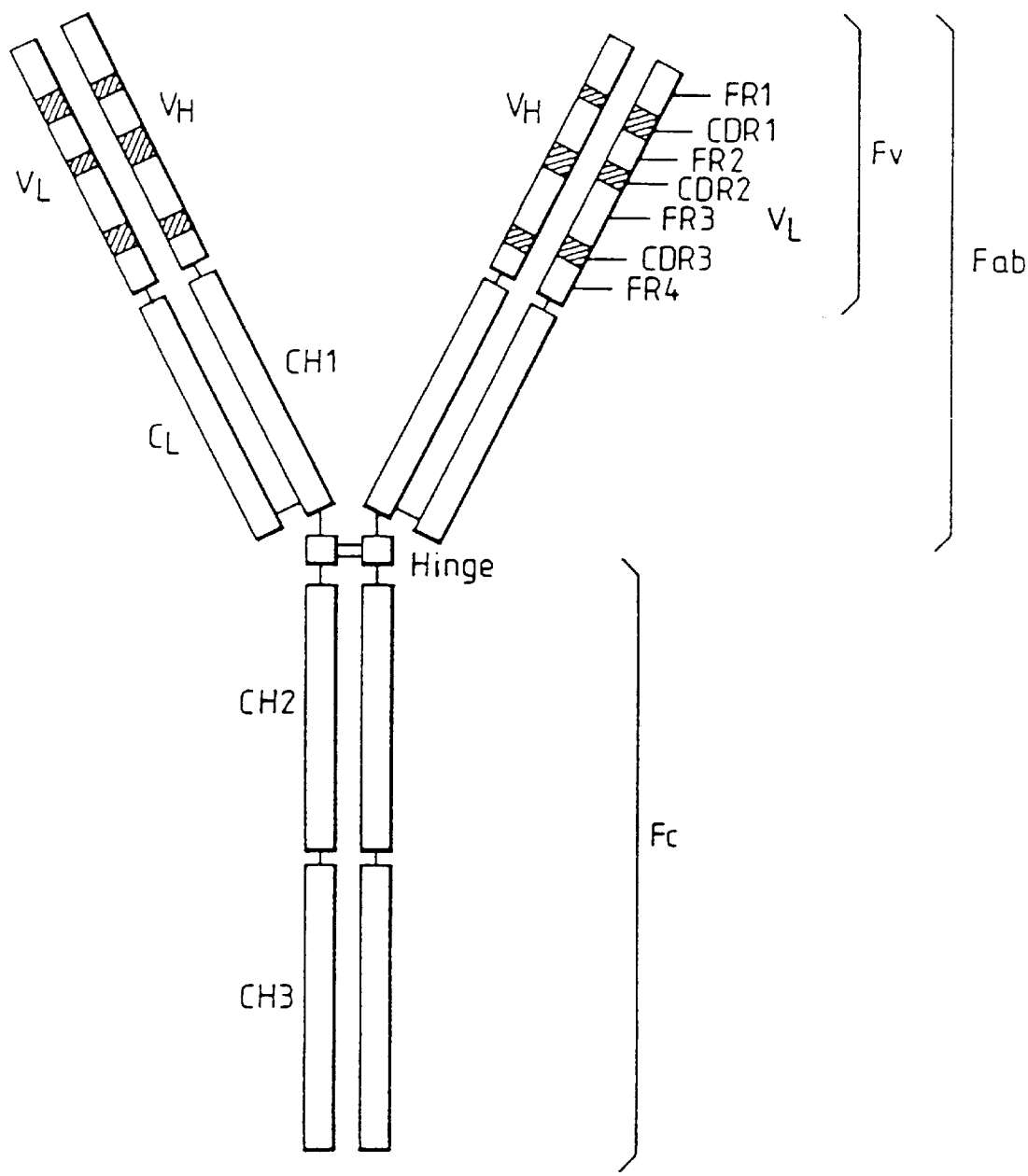

FIG. 14 depicts in diagramatic form the structure of a typical antibody (immunoglobulin) molecule.

Figure 15:
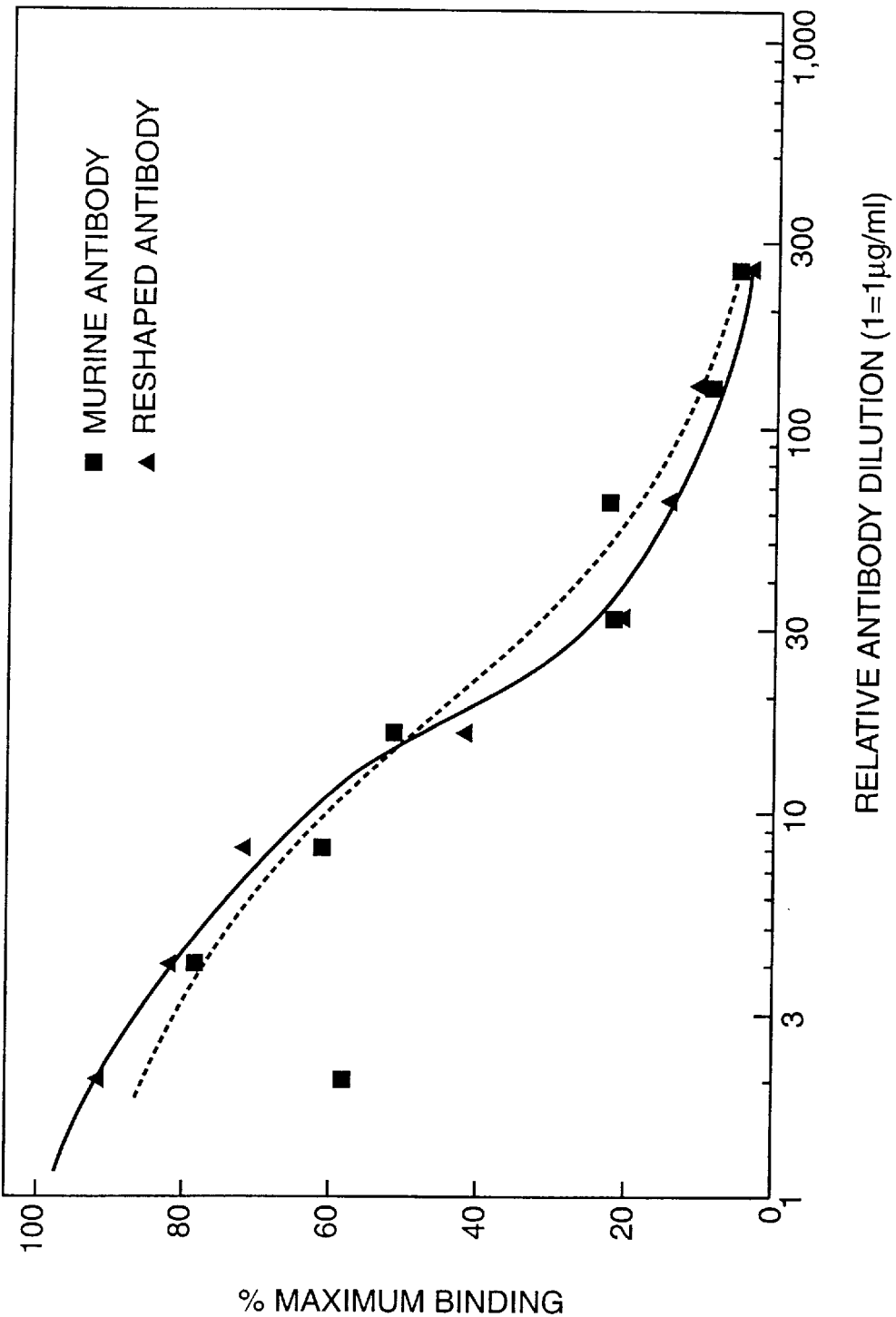

FIG. 15 shows in graphical form the relative specific anti-HMFG1 binding activity of the resulting reshaped human antibody.

The experimental procedures required to practice the invention do not in themselves represent unusual technology. The cloning and mutagenesis techniques were performed as generally described for example in Verhoeyen et al (1988); Riechmann et al (1988) and EP-A-239400 (Winter). The "de novo" synthesis of a reshaped human heavy chain variable region gene (see FIGS. 3a1–3d3) was done by conventional techniques, using a set of long overlapping oligonucleotides (see also Jones et al, 1988). Laboratory equipment and reagents for synthesising long oligonucleotides are readily available, and as techniques in this field develop it is becoming practicable to synthesise progressively longer sequences.

Detailed laboratory manuals, covering all basic aspects of recombinant DNA techniques, are available, e.g. "Molecular Cloning" by Sambrook et al (1989).

By means of the invention, the antigen binding regions of a mouse anti-HMFG antibody (HMFG1) were grafted onto human framework regions. The resulting reshaped human antibody (designated HuHMFG1) has binding characteristics similar to those of the original mouse antibody.

Such reshaped antibodies can be used for in vivo diagnosis and treatment of human cancers, eg. ovarian cancers and breast cancers, and are expected at least to reduce the problem of an immune response in the patient often seen upon administration of non-human antibody. A similar benefit has been shown for reshaped CAMPATH-1 antibody in Hale et al (1988).

Methods:
1. Cloning and sequence determination of the mouse variable region genes Messenger RNA was isolated from a murine hybridoma line which secretes the gamma-1, kappa anti-HMFG antibody "HMFG1" (see Taylor-Papadimitriou et al, 1981 and Arklie et al, 1981). First strand cDNA was synthesised by priming with oligonucleotides I and II (see FIG. 9) complementary to the 5' ends of the CH1 and Ck exons respectively. Second strand cDNA was obtained as described by Gübler and Hoffmann (1983).

Kinased EcoRI linkers were ligated to the heavy chain double-stranded cDNA and Pst1 linkers to the light chain double-stranded cDNA (both were first treated with EcoRI or PstI methylase to protect possible internal sites), followed by cloning into EcoRI or PstI-cut pUC9 (Vieira et al, 1982) and transformation of E. coli strain TG2 (Gibson, 1984).

Colonies containing genes coding for murine HMFG1 VH (MoVHHMFG1) and for murine anti-HMFG Vk (MoVkHMFG1) were identified by colony hybridisation with 2 probes consisting respectively of 32P-labelled first strand cDNA of HMFG1 VH and Vk. Positive clones were characterised by plasmid preparation, followed by EcoRI or PstI digestion and 1.5% agarose gel analysis. Full-size inserts (about 450 bp) were subcloned in the EcoRI or PstI site of M13mp18 (Norrander et al, 1983). This yielded clones with inserts in both orientations, facilitating nucleotide sequence determination of the entire insert, by the dideoxy chain termination method (Sanger et al, 1977).

The nucleotide sequences, and their translation into amino acid sequences, of the mature variable region genes MoVH-HMFG1 and MoVkHMFG1, are shown in FIGS. 1 and 2. The 450 bp inserts included a signal sequence and 5' untranslated sequences and linkers, not shown in the Figures.

2. Grafting of the mouse HMFG1 CDRs onto human framework regions

The general techniques necessary to achieve this have been described very adequately in Jones et al (1986), Verhoeyen et al (1988), Riechmann et al (1988) and in EP-A-239400 (Winter).

a) Light chain:

The basic construct used for reshaping a human light chain was M13mp9HuVkLYS (Riechmann et al, 1988), which contains framework regions with sequences based on those of the light chain variable regions of the human Bence-Jones protein REI (Epp et al, 1974).

The CDRs in this construct (FIG. 5a) were replaced by site-directed mutagenesis with oligonucleotides VI, VII and VIII encoding the HMFG1 kappa chain CDRs flanked by 12 nucleotides at each end encoding the corresponding human framework residues. These oligonucleotides are shown in FIG. 11. The mutagenesis was done as described in Riechmann et al (1988). The resulting reshaped human light chain variable region gene (HuVkHMFG1) is shown in FIG. 13.

b) Heavy chain:

A reshaped human heavy chain variable region gene was obtained by "de novo" synthesis. In the experiments published by Jones et al, etc, mentioned above, rodent heavy chain CDRs were grafted onto the framework regions of the human NEW heavy chain variable region. It was shown by Verhoeyen et al (1988) and by Riechmann et al (1988) that it is important that the human framework can support the rodent CDRs in a conformation similar to the one occurring in the original rodent antibody, and that certain CDR-framework interactions can be critical. It follows thus that the more dissimilar the rodent and the human framework sequences are, the less the chance will be for the CDR graft to "take".

Comparison of the heavy chain variable region amino acid sequence of the mouse HMFG1 (FIG. 1) to that of the human NEW (as used in Verhoeyen et al, 1988), revealed 44% differences between their respective framework regions. A much better homology was found when comparing to human heavy chain variable regions of subgroup I (Kabat et al, 1987); human VHNEW belongs to subgroup II.

We therefore decided to synthesise a human heavy chain variable region gene of subgroup I, containing the HMFG1heavy chain CDRs. We designed a consensus sequence for human heavy chain subgroup I variable regions, based on sequence information on this subgroup in Kabat et al, 1987. Optimal codon usage was taken from the sequences of mouse constant region genes (the genes are expressed in a mouse myeloma line).

There are only 14% differences between the framework sequences of the HMFG1 VH and the VH of this human VH subgroup I consensus sequence (HuVHIcon). The resulting reshaped gene was designated the name HuVHIconHMFG1, and is depicted in FIG. 12. The gene synthesis is described separately in section (c) below. The newly synthesised gene HuVHIconHMFG1 was used to replace HUVHLYS in the construct M13mp9HuVHLYS (Verhoeyen et al, 1988), yielding the vector M13mp9HuVHIconHMFG1 (see FIG. 4a).

3. Assembly of reshaped human-antibody genes in expression vectors

The next stage involved the use of a murine heavy chain enhancer IgEnh, described in Neuberger et al (1983) where the enhancer is contained in a 1 kb Xbal fragment of plasmid PSV-Vµ1. The 700 bp Xbal/EcoRI subfragment of this 1 kb Xbal fragment is sufficient to confer enhancer activity.

An alternative source of this enhancer is plasmid psV-neoHuVkPLAP (see FIG. 5a), a variation of which has been deposited in an *E. coli* strain under the Budapest Treaty on Apr. 19, 1990 as NCTC 12390. As deposited, the plasmid also contains a human kappa-chain constant region gene (cloned in the BamH1 site).

The reshaped human genes as prepared in sections 2(a) and 2(b) above, were excised from the M13 vectors as HindIII—BamHI fragments. The heavy chain variable region genes were cloned into a vector based on pSV2gpt (Mulligan et al, 1981) and the light chain variable region genes cloned into a vector based on pSV2neo (Southern et al, 1981) expression vectors, both containing the immunoglobulin heavy chain enhancer IgEnh. In the pSV2gpt based antibody expression vector (see FIG. 4b–4c), the Xbal/EcoRI enhancer containing fragment was cloned in the unique EcoRI site of the pSV2gpt vector (after ligating EcoRI linkers to the filled in Xbal end of the fragment).

In the pSVneo based antibody expression vector (see FIG. 5a–5b), the 1 kb Xbal enhancer containing fragment was first cloned into pUC12 (Vieira et al, 1982), yielding the plasmid pUC12-IgEnh, see FIG. 6. The enhancer can then be cut out as a 700 bp EcoRI/HindIII fragment (either orientation of the enhancer will work). This 700 bp EcoRI/HindIII fragment is present in the plasmid pSVneoHuVkPLAP, that we used to clone the HuVkHMFG1-containing fragment described in section 2a, see FIG. 5a and 5b. The HindIII site in the original pSV2neo had been removed. It is possible to use pSV2gpt as an alternative vector for light chain expression, as in practice there is no need for neo selection.

The HuVHIconMFG1 gene was linked to a human gamma 1 constant region (Takahashi et al, 1982), cloned initially as a 8 kb HindIII fragment into the HindIII site of pBGS18 (Spratt et al, 1986), and then in the pSV2gpt expression vector as a BamHI fragment (see FIGS. 4d and 7). It should be noted that in the Takahashi et al (1982) reference there is an error in FIG. 1: the last (3') two sites are BamH1 followed by HindIII, and not the converse. This was confirmed by Flanagan et al (1982).

The HuVkHMFG1 gene was linked to a human C kappa constant region (Hieter et al, 1980) also cloned in as a BamHI fragment (see FIGS. 5b and 8). The source of the human Ck used in FIG. 8 is given in Hieter et al (1980). The 12 kb BamH1 fragment from embryonic DNA (cloned in a gamma Ch28 vector system) was subcloned in the BamH1 site of plasmid pBR322.

4. "de novo" synthesis of the HuVHIconHMFG1 gene

We decided to synthesise a gene encoding a human variable region gene of subgroup I (Kabat et al, 1987), and with the-CDRs of VHHMFG1 (FIG. 1). In summary, the synthetic gene is designed in such a way that it can substitute the HuVHLYS gene in the existing M13mp9HuVHLYS vector. The M13mp9HuVHLYS was mutagenized to contain a KpnI and SalI site at the appropriate places (see also FIG. 4a), to enable cloning of the newly synthesized gene as a KpnI-SalI fragment.

The gene sequence was designed as described above in section 2(b) and is depicted in FIG. 12. To facilitate the substitution of this gene for the HUVHLYS gene in M13mp9HuVHLYS (Verhoeyen et al, 1988, see also FIG. 4a), 5' and 3' extensions were added to the gene. The 5' extension contains 37 bp of the leader intron and 11 bp of the second half of the leader exon (as in M13mp9HuVHLYS), and has a KpnI site at the very 5' end. The 3' extension contains 38 untranslated nucleotides (as in M13mp9HuVHLYS) and ends in a SalI site.

M13mp9HuVHLYS was modified by site directed mutagenesis with oligonucleotides III and IV to contain a KpnI and SalI site at the appropriate places (see FIG. 4a and FIG. 10). This vector was named M13mp9HuVHLYS(K,S). This enabled cloning of the HuVHIconHMFG1 gene as a KpnI-SalI fragment in KpnI-SalI cut M13mp9HuVHLYS (K,S) vector.

For practical reasons it was decided to synthesise the gene as three fragments (cassettes), which were then assembled in one complete gene.

Each fragment contains one of the three VHHMFG1 CDRS, and can easily be cloned or removed by using the (existing or newly introduced) unique restriction sites (see FIG. 3a). Each fragment was elongated at the 5' and 3' end to create a HindIII and BamHI site respectively, to enable cloning in pEMBL9 (Dente et al, 1983). The coding strand of each fragment was divided in oligonucleotides with an average length of 33 bases. The same was done for the non-coding strand, in such a way that the oligonucleotides overlapped approximately 50% with those of the coding strand.

The sequences of each fragment and of the oligonucleotides used for assembly, are shown in FIGS. 3b, 3c and 3d.

Before assembling the fragments, the 5' ends of the synthetic oligonucleotides had to be phosphorylated in order to facilitate ligation. Phosphorylation was performed as follows: equimolar amounts (50 pmol) of the oligonucleotides were pooled and kinased in 40 µl reaction buffer with 8 units polynucleotide kinase for 30–45 minutes at 37° C. The reaction was stopped by heating for 5 minutes at 70° C. and ethanol precipitation. Annealing was done by dissolving the pellet in 30 µl of a buffer containing: 7 mM TrisCl pH 7.5, 10 mM 2-mercapto-ethanol, 5 mM ATP were added. Subsequently the mixture was placed in a waterbath at 65° C. for 5 minutes, followed by cooling to 30° C. over a period of 1 hour. MgCl2 was added to a final concentration of 10 mM. T4 DNA-ligase (2.5 units) was added and the mixture was placed at 37° C. for 30 min. (or overnight at 16° C.). After this the reaction mixture was heated for 10 minutes at 70° C. After ethanol precipitation the pellet was dissolved in digestion buffer and cut with HindIII and BamHI. The mixture was separated on a 2% agarose gel and the fragment with a length corresponding to the correctly assembled cassette was isolated by electro-elution.

The fragments (1, 2, 3) were ligated in pEMBL9 (cut with HindIII/BamHI), yielding the vectors pUR4107, pUR4108 and pUR4109 respectively. The sequence of the inserts was checked by sequence analysis (in both orientations). Fragment 1 was isolated from pUR4107 by KpnI/XhoI digestion, whilst fragment 2 was isolated from pUR4108 by XhoI/SacI digestion, after which they were ligated in KpnI/SacI cut pUR4109 in a three-fragment ligation. The resulting plasmid was named pUR4110 (see FIG. 4a). Sequencing analysis showed that the insert contained the desired HuVHIcon-HMFG1 gene. This gene was cloned in a pSV2gpt-derived expression vector as depicted in FIGS. 4b and 4c. The vector pSVgptMoVHLYS-MoIgG1 (Verhoeyen et al, 1988) was used as the source of a pSVgpt-based vector containing the IgEnh enhancer.

5. Expression in myeloma cells

Co-transfection of the expression plasmids pSVgptHuVHIconHMFG1-HuIgG1 and pSVneoHuVkHMFG1-HuCk (FIGS. 4d and 5b) into NSO myeloma cells was done by electroporation (Potter et al, 1984), after linearisation with PvuI. Transfectomas were selected in mycophenolic acid containing medium to select for cells expressing the gpt gene product, and screened for antibody production and anti-HMFG activity by ELISA assays.

Clones positive for both assays were obtained and subcloned by limiting dilution and pure clones were assayed again for anti-HMFG activity, and the best producing clones were grown in serum-free medium for antibody production.

6. Deposited plasmids

E. coli strains containing plasmids used in the above procedure have been deposited, in accordance with the provisions of the Budapest Treaty, in the National Collection of Type Cultures, Central Public Health Laboratory, 61 Colindal Avenue London, NW9 5HT, United Kingdom, on Jul. 11, 1990 as follows:

NCTC 12411: K12, TG1 E. coli containing plasmid pSVgptHuVHIconHMFG1-HuIgG1 (identified for the purposes of deposition simply as pSVgpt-HuVHHMFG1-HuIgG1)

NCTC 12412: K12, TG1 E. coli containing plasmid pSVneo-HuVkHMFG1-HuCk

7. Binding ability of the reshaped human antibodies

A useful way of demonstrating binding ability of the reshaped antibody is to show that it has a similar antibody dilution curve when binding to antigen adsorbed on a solid surface. Such curves were generated as follows, using the parent murine anti-HMFG antibody and a reshaped human antibody prepared by the foregoing procedure.

0.5 ml of 10% w/v M280 tosyl activated magnetic beads (Dynal, Wirral, UK) were coupled to milk mucin (106 units as determined in an immunoassay for HMFG1 in which normal human serum registers 100–200 units per ml). Milk mucin was prepared from human breast milk according to the method of Burchell et al (1987). The level of mucin was chosen to provide suitable activity for the assays in which the beads were used. The coupling was in 2.5 ml of 0.5M borate buffer at pH 9.5 plus 2.5 ml of mucin in phosphate-buffered saline pH 7.2 (PBS) for 22 hrs at 37° C. with gentle rotation. Blocking of remaining active sites was accomplished by adding 1 ml of 10% bovine serum albumen (BSA; Sigma) in PBSA (PBS+0.02% sodium azide followed by a further 7 hr incubation at 37° C. The excess protein was washed away after using a samarium cobalt magnet to pellet the beads. Further washing was 3× in wash buffer (0.1M potassium phosphate pH 8.0, 0.1% Tween 20, 0.5% BSA) and 4× in rinse buffer (PBS+0.1% BSA, 0.1% merthiolate). Beads were stored in rinse buffer at 10% w/v (estimated by dry weight analysis).

Antibody binding was measured from a series of doubling dilutions of antibody samples (prepared by weighing in critical cases). 50 µl samples were incubated in replicate in microtitre wells with 50 µl of 0.05% w/v suspension of beads in 1% BSA/PBSM (PBS+0.01% merthiolate) at room temperature for 1 hr on a plate shaker. Small cobalt samarium magnets, embedded in a plastic base, were used to sediment the beads to the sides of the wells of the plate to allow liquid removal and washing once with 150 µl PBSTM (PBSM+0.15% Tween 20). This was followed by detection of bound antibody with 50 µl of alkaline phosphatase coupled goat anti-human IgG (H+L) (Jackson) used at $\frac{1}{1000}$ dilution in 1% BSA in PBSTM for 1 hr at room temperature. The beads were washed 3× in PBSTM. Colour development was with 200 µl of nitro phenyl phosphate (Sigma alkaline phosphatase substrate tablets) in 1M diethanolamine buffer at pH 9.8. Optical densities were read in a Dynatech plate reader at 410 nm after transferring fixed volumes of supernatant (usually 150 µl) to a flat bottom well microtitre plate. For examination of mouse antibodies the conjugate used was rabbit anti-mouse IgG (Sigma).

Antibody-dilution curves for the murine and reshaped HMFG1 antibodies are shown in FIG. 15. Maximum binding was determined with a large excess of antibody and negative controls had none. Antibody concentrations, in µg/ml, were determined by UV absorption measurements at 280 nm. For both antibodies a dilution of 1 has been set equivalent to 1 µg/ml. The two curves are similar, indicating a significant and useful level of binding effectiveness for the reshaped antibody of the invention.

References:
Arklie et al (1981)—*Int. J. Cancer,* 28, p.23–29
Burchell et al (1987)—*Cancer Res.,* 47, p.5476
Dente et al (1983)—*Nucleic Acids Res.* II, p.1645–1655
Epp et al (1974)—*Eur. J. Biochem.* 45, p.513–524
Flanagan et al (1982)—*Nature,* 300, p.709–713
Gendler et al (1988)—*J. Biol. Chem,* 236, p.12820–12823
Gibson T (1984)—PhD thesis, LMB-MRC Cambridge
Gubler et al (1983)—*Gene,* 25, p.263–269
Hale et al (1988)—*Lancet,* 2, p.1394
Hieter et al (1980)—*Cell,* 22, p.197–207
Jones et al (1986)—*Nature,* 321, p.522–525
Kabat et al (1987)—in *Sequences of Proteins of Immunological Interest,* p.ix -US Dept of Health and Human Services
Mulligan et al (1981)—*Proc. natn. Acad. Sci. U.S.A.,* 78 p.2072–2076
Neuberger et al (1983)—*EMBO Journal,* 2, p.1373–1378
Norrander et al (1983)—*Gene,* 26, p.101–106
Potter et al (1984)—*PNAS,* 81, p.7161–7163
Riechmann et al (1988)—*Nature,* 332, p.323–327
Sambrook et al (1989)—*Molecular Cloning,* 2nd Edition, Cold Spring Harbour Laboratory Press, New York
Sanger et al (1977)—*PNAS USA,* 74, p.5463–5467
Saul et al (1978)—*J. biol. Chem.* 253, p.585–597
Southern et al (1981)—*J. molec. appl. Genetics,* 1 p.327–345

Spratt et al (1936)—*Gene,* 41, p.337–342
Takahashi et al (1982)—*Cell,* 29, p.671–679
Taylor-Papadimitrion et al (1981)—*Int. J. Cancer,* 28, p.17–21
Verhoeyen et al (1988)—*Science,* 239, p.1534–1536
Vieira et al (1982)—*Gene,* 19, p.259–268
Winter (1987)—EP-A-239400
Xing et al (1990)—EP-A2-369816

What is claimed is:

1. An antibody or antibody fragment having specificity for human polymorphic endothelial mucia (PEM), said antibody or fragment incorporating a heavy chain variable region comprising the amino acid sequence represented by SEQ ID NO:60 and a light chain variable region comprising the amino acid sequence represented by SEQ ID NO:62.

2. An antibody or antibody fragment according to claim 1, wherein the PEM is human milk fat globule (HMFG).

3. A stable host cell line producing an antibody or antibody fragment according to claim 1, resulting from incorporation in the cell line of foreign nucleic acid encoding the antibody or antibody fragment.

4. A stable host cell line according to claim 3, wherein the nucleic acid includes one or more of the nucleotide sequences:
 i) GCC TAC TGG ATA GAG;
 ii) GAG ATT TTA CCT GGA AGT AAT AAT TCT AGA TAC AAT GAG AAG TTC AAG GGC;
 iii) TCC TAC GAC TTT GCC TGG TTT GCT TAC;
 iv) AAG TCC AGT CAG AGC CTT TTA TAT AGT AGC AAT CAA AAG ATC TAC TTG OCC;
 v) TGG GCA TCC ACT AGG GAA TCT; and
 vi) CAG CAA TAT TAT AGA TAT CCT CGG ACG.

5. A stable host cell line comprising a nucleic acid molecule represented by SEQ ID NO:59.

6. A stable host cell line comprising a nucleic acid molecule represented by SEQ ID NO:61.

7. A stable host cell line comprising a nucleic acid molecule that encodes amino acid sequence SEQ ID NO:60.

8. A stable host cell line comprising a nucleic acid molecule that encodes amino acid sequence SEQ ID NO:62.

9. Plasmid pSVgpt-HuVG-1-HuIgG1, deposited as NCTC 12411.

10. Plasmid pSVneo-HuVkHMG1-HuCk, deposited as NCTC 1241.

11. A method of producing an antibody by expressing the plasmids pSVgpt-HuVHHMFG-1-HuIgG1 deposited as NCTC 12411, and pSVneo-HuVkHMFG1-HuCk, deposited as NCTC 12412, thereby producing said antibody.

12. *E. coli* NCTC 12411.

13. *E. coli* NCTC 12412.

14. A DNA molecule encoding an antibody heavy-chain variable region having specificity for HMFG, as contained in *E. coli* NCTC 12411.

15. A DNA molecule encoding an antibody light-chain variable region having specificity for HMFG, as contained in *E. coli* NCTC 12412.

16. An antibody or antigen binding fragment thereof, comprising at least one light chain variable region comprising the sequence represented by SEQ ID NO:60 and one heavy chain variable region comprising the sequence represented by SEQ ID NO:62.

17. An antibody or antibody fragment according to claim 14, linked to or incorporating an agent capable of retarding or terminating the growth of cancerous cells, or linked to an agent capable of being detected while inside the human body.

18. An injectable composition comprising an antibody or antibody fragment according to claim 17, in a pharmaceutically acceptable carrier.

19. A method for human cancer therapy or imaging that comprises administering an antibody or antibody fragment according to claim 17 to an individual.

20. A diagnostic composition for in-vivo use in humans comprising an antibody or fragment according to claim 1 in a carrier.

21. A method for the diagnosis of cancer which comprises administering a composition according to claim 20 to a patient.

* * * * *

```
                          SEQUENCE LISTING (1) GENERAL INFORMATION:

(iii) NUMBER OF SEQUENCES: 62

(2) INFORMATION FOR SEQ ID NO:1:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:1:

Ala Tyr Trp Ile Glu
1               5

(2) INFORMATION FOR SEQ ID NO:2:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Glu Ile Leu Pro Gly Ser Asn Asn Ser Arg Tyr Asn Glu Lys Phe Lys
1               5                   10                  15

Gly (2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Ser Tyr Asp Phe Ala Trp Phe Ala Tyr
1               5

(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: cDNA
```

(xi) SEQUENCE DESCRIPTION: SEQ ID NO:4:

Lys Ser Ser Gln Ser Leu Leu Tyr Ser Ser Asn Gln Lys Ile Tyr Leu
1               5                   10                  15
Ala (2) INFORMATION FOR SEQ ID NO:5:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:5:

Trp Ala Ser Thr Arg Glu Ser
1               5

(2) INFORMATION FOR SEQ ID NO:6:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:6:

Gln Gln Tyr Tyr Arg Tyr Pro Arg Thr
1               5

(2) INFORMATION FOR SEQ ID NO:7:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:7:

GCCTACTGGA TAGAG                                                    15

(2) INFORMATION FOR SEQ ID NO:8:

(i) SEQUENCE CHARACTERISTICS:
            (A) LENGTH: 51 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

GAGATTTTAC CTGGAAGTAA TAATTCTAGA TACAATGAGA AGTTCAAGGG C             51

(2) INFORMATION FOR SEQ ID NO:9:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:9:

TCCTACGACT TTGCCTGGTT TGCTTAC                                           27

(2) INFORMATION FOR SEQ ID NO:10:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

AAGTCCAGTC AGAGCCTTTT ATATAGTAGC AATCAAAAGA TCTACTTGGC C               51

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

TGGGCATCCA CTAGGGAATC T                                                 21

(2) INFORMATION FOR SEQ ID NO:12:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

CAGCAATATT ATAGATATCC TCGGACG                                           27

(2) INFORMATION FOR SEQ ID NO:13:

(i) SEQUENCE CHARACTERISTICS:
        (A) LENGTH: 354 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:13:

CAGGTTCAGC TGCAGCAGTC TGGAGCTGAG CTGATGAAGC CTGGGGCCTC AGTGAAGATA      60

TCCTGCAAGG CTACTGGCTA CACATTCAGT GCCTACTGGA TAGAGTGGGT AAAGCAGAGG      120

CCTGGACATG GCCTTGAGTG GATTGGAGAG ATTTTACCTG GAAGTAATAA TTCTAGATAC      180

AATGAGAAGT TCAAGGGCAA GGCCACATTC ACTGCTGATA CATCCTCCAA CACAGCCTAC      240

ATGCAACTCA GCAGCCTGAC ATCTGAGGAC TCTGCCGTCT ATTACTGTTC AAGGTCCTAC      300

GACTTTGCCT GGTTTGCTTA CTGGGGCCAA GGGACTCCGG TCACTGTCTC TGCA            354

(2) INFORMATION FOR SEQ ID NO:14:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

```
Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ala Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Asn Asn Ser Arg Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ser Arg Ser Tyr Asp Phe Ala Trp Phe Ala Tyr Trp Gly Gln Gly Thr
            100                 105                 110

Pro Val Thr Val Ser Ala
        115
```

(2) INFORMATION FOR SEQ ID NO:15:

(i) SEQUENCE CHARACTERISTICS:
        (A) LENGTH: 342 base pairs
        (B) TYPE: nucleic acid
        (C) STRANDEDNESS: both
        (D) TOPOLOGY: linear (ii) MOLECULE TYPE: protein (xi) SEQUENCE DESCRIPTION: SEQ ID NO:15:

```
GACATTGTGA TGTCACAGTC TCCATCCTCC CTAGCTGTGT CAGTTGGAGA GAAGGTTACT    60

ATGAGCTGCA AGTCCAGTCA GAGCCTTTTA TATAGTAGCA ATCAAAAGAT CTACTTGGCC   120

TGGTACCAGC AGAAACCAGG GCAGTCTCCT AAACTGCTGA TTTACTGGGC ATCCACTAGG   180

GAATCTGGGG TCCCTGATCG CTTCACAGGC GGTGGATCTG GGACAGATTT CACTCTCACC   240

ATCAGCAGTG TGAAGGCTGA AGACCTGGCA GTTTATTACT GTCAGCAATA TTATAGATAT   300

CCTCGGACGT TCGGTGGAGG CACCAAGCTG GAAATCAAAC GG                      342
```

(2) INFORMATION FOR SEQ ID NO:16:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: cDNA (xi) SEQUENCE DESCRIPTION: SEQ ID NO:16:

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30
```

```
Ser Asn Gln Lys Ile Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
 50                  55                  60

Pro Asp Arg Phe Thr Gly Gly Ser Gly Thr Asp Phe Thr Leu Thr
 65              70                  75                  80

Ile Ser Ser Val Lys Ala Glu Asp Leu Ala Val Tyr Tyr Cys Gln Gln
                 85                  90                  95

Tyr Tyr Arg Tyr Pro Arg Thr Phe Gly Gly Gly Thr Lys Leu Glu Ile
             100                 105                 110

Lys Arg (2) INFORMATION FOR SEQ ID NO:17:

(i) SEQUENCE CHARACTERISTICS:
        (A) LENGTH: 240 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:17:

ACAGTAGCAG GCTTGAGGAA AGCTTCTATA TATGGGTACC AATGACATCC ACTTTGCCTT      60

TCTCTCCACA GGTGTCCACT CCCAGGTGCA GCTGGTGCAG TCTGGGGCAG AGGTGAAAAA    120

GCCTGGGGCC TCAGTGAAGG TCTCCTGCAA GGCTTCTGGC TACACCTTCA GTGCCTACTG    180

GATAGAGTGG GTGCGCCAGG CTCCAGGAAA GGGCCTCGAG TGGGTCGGAT CCAGGGAGAT    240

(2) INFORMATION FOR SEQ ID NO:18:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:18:

AGCTTCTATA TATGGGTACC AATGACATCC AC                                   32

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

TTTGCCTTTC TCTCCACAGG TGTCCACTCC CAG                                  33

(2) INFORMATION FOR SEQ ID NO:20:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:20:

GTGCAGCTGG TGCAGTCTGG GGCAGAGGTG AAAAAG                36

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

CCTGGGGCCT CAGTGAAGGT GTCCTGCAAG GCT                   33

(2) INFORMATION FOR SEQ ID NO:22:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

TCTGGCTACA CCTTCAGTGC CTACTGGATA GAGTGG                36

(2) INFORMATION FOR SEQ ID NO:23:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GTGCGCCAGG CTCCAGGAAA GGGCCTCGAG TGGGTCG               37

(2) INFORMATION FOR SEQ ID NO:24:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:24:

GAGAAAGGCA AAGTGGATGT CATTGGTACC CATATATAGA            40

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CTGCACCAGC TGCACCTGGG AGTGGACACC TGTGGA                36

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

```
TGAGGCCCCA GGCTTTTTCA CCTCTGCCCC AGA                          33
```

(2) INFORMATION FOR SEQ ID NO:27:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

```
GGTGTAGCCA GAAGCCTTGC AGGACACCTT CAC                          33
```

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

```
AGCCTGGCGC ACCCACTCTA TCCAGTAGGC ACTGAA                       36
```

(2) INFORMATION FOR SEQ ID NO:29:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

```
GATCCGACCC ACTCGAGGCC CTTTCCTGG                               29
```

(2) INFORMATION FOR SEQ ID NO:30:

(i) SEQUENCE CHARACTERISTICS:
        (A) LENGTH: 180 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:30:

```
GACAGCCGTA GAGTGGGTGC AAGCTTCTCC AGGACTCGAG TGGGTCGGAG AGATTTTACC    60
TGGAAGTAAT AATTCTAGAT ACAATGAGAA GTTCAAGGGC CGAGTGACAG TCACTAGAGA   120
CACATCCACA AACACAGCCT ACATGGAGCT CAGCAGCCTG AGGATCCAGC AGCCTGAGGT   180
```

(2) INFORMATION FOR SEQ ID NO:31:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

AGCTTCTCCA GGACTCGAGT GGGTC        25

(2) INFORMATION FOR SEQ ID NO:32:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

GGAGAGATTT TACCTGGAAG TAATAAT        27

(2) INFORMATION FOR SEQ ID NO:33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

TCTAGATACA ATGAGAAGTT CAAGGGCCGA GTGACAGTC        39

(2) INFORMATION FOR SEQ ID NO:34:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

ACTAGAGACA CATCCACAAA CACAGCCTAC        30

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

ATGGAGCTCA GCAGCCTGAG        20

(2) INFORMATION FOR SEQ ID NO:36:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

```
AGGTAAAATC TCTCCGACCC ACTCGAGTCC TGGAGA                    36
```

(2) INFORMATION FOR SEQ ID NO:37:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

```
GCCCTTGAAC TTCTCATTGT ATCTAGAATT ATTACTTCC                 39
```

(2) INFORMATION FOR SEQ ID NO:38:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

```
TGTGTCTCTA GTGACTGTCA CTCG                                 24
```

(2) INFORMATION FOR SEQ ID NO:39:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:39:

```
GATCCTCAGG CTGCTGAGCT CCATGTAGGC TGTGTTTGTG GA             42
```

(2) INFORMATION FOR SEQ ID NO:40:

(i) SEQUENCE CHARACTERISTICS:
        (A) LENGTH: 190 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:40:

```
CACATCCACA AGCTTAAACA CAGCCGAGCT CAGCAGCCTG AGGTCTGAGG ACACAGCCGT      60
CTATTACTGT GCAAGATCCT ACGACTTTGC CTGGTTTGCT TACTGGGGCC AAGGGACTCT     120
GGTCACAGTC TCCTCAGGTG AGTCCTTACA ACCTCTCTCT TCTATTCAGT CGACATAGAT     180
ACGTGGATCC                                                           190
```

(2) INFORMATION FOR SEQ ID NO:41:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:41:

AGCTTAAACA CAGCCGAGCT CAGCAGCCTG AGGTCTGAG                    39

(2) INFORMATION FOR SEQ ID NO:42:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:42:

GACACAGCCG TCTATTACTG TGCAAGA                              27

(2) INFORMATION FOR SEQ ID NO:43:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:43:

TCCTACGACT TTGCCTGGTT TGCTTACTGG GGCCAAGGG                    39

(2) INFORMATION FOR SEQ ID NO:44:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:44:

ACTCTGGTCA CAGTCTCCTC AGGTGAGTCC TTACAACCT                    39

(2) INFORMATION FOR SEQ ID NO:45:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:45:

CTCTCTTCTA TTCAGTCGAC ATAGATACGT G                          31

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:46:

GAGCTCGGCT GTGTTTA                                                              17

(2) INFORMATION FOR SEQ ID NO:47:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:47:

ATAGACGGCT GTGTCCTCAG ACCTCAGGCT GCT                                            33

(2) INFORMATION FOR SEQ ID NO:48:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:48:

GTAAGCAAAC CAGGCAAAGT CGTAGGATCT TGCACAGTA                                      39

(2) INFORMATION FOR SEQ ID NO:49:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:49:

ACCTGAGGAG ACTGTGACCA GAGTCCCTTG GCCCCA                                         36

(2) INFORMATION FOR SEQ ID NO:50:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:50:

TGAATAGAAG AGAGAGGTTG TAAGGACTC                                                 29

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:51:

GATCCACGTA TCTATGTCGA C                                             21

(2) INFORMATION FOR SEQ ID NO:52:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:52:

GATAGACAGA TGGGGGTGTC GTTT                                     24

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:53:

AGATGGATAC AGTTGGTGCA GCAT                                     24

(2) INFORMATION FOR SEQ ID NO:54:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:54:

TGTCATTGGT ACCCATAT                                                   18

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:55:

AAATCTATGT CGACTGAATA G                                             21

(2) INFORMATION FOR SEQ ID NO:56:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:56:

```
CTGCTGGTAC CAGGCCAAGT AGATCTTTTG ATTGCTACTA TATAAAGGC TCTGACTGGA      60

CTTACAGGTG ATGGT                                                      75
```

(2) INFORMATION FOR SEQ ID NO:57:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:57:

```
GCTTGGCACA CCAGATTCCC TAGTGGATGC CCAGTAGATC AGCAG                     45
```

(2) INFORMATION FOR SEQ ID NO:58:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:58:

```
CCCTTGGCCG AACGTCCGAG GATATCTATA ATATTGCTGG CAGTAGTAGG T              51
```

(2) INFORMATION FOR SEQ ID NO:59:

(i) SEQUENCE CHARACTERISTICS:
        (A) LENGTH: 354 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:59:

```
CAGGTGCAGC TGGTGCAGTC TGGGGCAGAG GTGAAAAAGC CTGGGGCCTC AGTGAAGGTG     60

TCCTGCAAGG CTTCTGGCTA CACCTTCAGT GCCTACTGGA TAGAGTGGGT GCGCCAGGCT    120

CCAGGAAAGG GCCTCGAGTG GGTCGGAGAG ATTTTACCTG GAAGTAATAA TTCTAGATAC    180

AATGAGAAGT TCAAGGGCCG AGTGACAGTC ACTAGAGACA CATCCACAAA CACAGCCTAC    240

ATGGAGCTCA GCAGCCTGAG GTCTGAGGAC ACAGCCGTCT ATTACTGTGC AAGATCCTAC    300

GACTTTGCCT GGTTTGCTTA CTGGGGCCAA GGGACTCTGG TCACAGTCTC CTCA          354
```

(2) INFORMATION FOR SEQ ID NO:60:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

Gln Val Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Lys Gly Leu Glu Trp Val
        35                  40                  45

Gly Glu Ile Leu Pro Gly Ser Asn Asn Ser Arg Tyr Asn Glu Lys Phe
    50                  55                  60

Lys Gly Arg Val Thr Val Thr Arg Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Asp Phe Ala Trp Phe Ala Tyr Trp Gly Gln Gly Thr
            100                 105                 110

Leu Val Thr Val Ser Ser
        115

(2) INFORMATION FOR SEQ ID NO:61:

(i) SEQUENCE CHARACTERISTICS:
        (A) LENGTH: 342 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:61:

GACATCCAGA TGACCCAGAG CCCAAGCAGC CTGAGCGCCA GCGTGGGTGA CAGAGTGACC      60

ATCACCTGTA AGTCCAGTCA GAGCCTTTTA TATAGTAGCA ATCAAAAGAT CTACTTGGCC     120

TGGTACCAGC AGAAGCCAGG TAAGGCTCCA AAGCTGCTGA TCTACTGGGC ATCCACTAGG     180

GAATCTGGTG TGCCAAGCAG ATTCAGCGGT AGCGGTAGCG GTACCGACTT CACCTTCACC     240

ATCAGCAGCC TCCAGCCAGA GGACATCGCC ACCTACTACT GCCAGCAATA TTATAGATAT     300

CCTCGGACGT TCGGCCAAGG GACCAAGGTG GAAATCAAAC GT                        342

(2) INFORMATION FOR SEQ ID NO:62:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:62:

Asp Ile Gln Met Thr Gln Ser Pro Ser Ser Leu Ser Ala Ser Val Gly
1               5                  10                  15

Asp Arg Val Thr Ile Thr Cys Lys Ser Ser Gln Ser Leu Leu Tyr Ser
            20                  25                  30

Ser Asn Gln Lys Ile Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

```
                                    -continued
Pro Ser Arg Phe Ser Gly Ser Gly Ser Gly Thr Asp Phe Thr Phe Thr
65              70              75                  80

Ile Ser Ser Leu Gln Pro Glu Asp Ile Ala Thr Tyr Tyr Cys Gln Gln
                85              90                  95

Tyr Tyr Arg Tyr Pro Arg Thr Phe Gly Gln Gly Thr Lys Val Glu Ile
            100             105                 110

Lys Arg
```